United States Patent
Ishikura

(10) Patent No.: US 9,910,052 B2
(45) Date of Patent: Mar. 6, 2018

(54) METHOD OF DIAGNOSING AND TREATING INFECTIOUS DISSEMINATED INTRAVASCULAR COAGULATION

(71) Applicants: LSI MEDIENCE CORPORATION, Tokyo (JP); FUKUOKA UNIVERSITY, Fukuoka (JP)

(72) Inventor: Hiroyasu Ishikura, Fukuoka (JP)

(73) Assignees: LSI MEDIENCE CORPORATION, Tokyo (JP); FUKUOKA UNIVERSITY, Fukuoka (JP)

( * ) Notice: Subject to any disclaimer, the term of this patent is extended or adjusted under 35 U.S.C. 154(b) by 465 days.

(21) Appl. No.: 14/398,971

(22) PCT Filed: Apr. 26, 2013

(86) PCT No.: PCT/JP2013/062352
§ 371 (c)(1),
(2) Date: Nov. 4, 2014

(87) PCT Pub. No.: WO2013/168602
PCT Pub. Date: Nov. 14, 2013

(65) Prior Publication Data
US 2015/0118699 A1    Apr. 30, 2015

(30) Foreign Application Priority Data

May 7, 2012  (JP) ................. 2012-106216
May 7, 2012  (JP) ................. 2012-106217

(51) Int. Cl.
| | |
|---|---|
| G01N 31/00 | (2006.01) |
| G01N 33/53 | (2006.01) |
| G01N 33/86 | (2006.01) |
| C07K 14/705 | (2006.01) |
| G01N 33/68 | (2006.01) |
| C12Q 1/56 | (2006.01) |

(52) U.S. Cl.
CPC ....... *G01N 33/86* (2013.01); *C07K 14/70596* (2013.01); *C12Q 1/56* (2013.01); *G01N 33/6893* (2013.01); *G01N 2333/70596* (2013.01); *G01N 2800/224* (2013.01)

(58) Field of Classification Search
None
See application file for complete search history.

(56) References Cited

U.S. PATENT DOCUMENTS

| | | |
|---|---|---|
| 2004/0248308 A1 | 12/2004 | Toh et al. |
| 2008/0096221 A1 | 4/2008 | Ono |
| 2009/0004673 A1 | 1/2009 | Ono et al. |
| 2013/0288276 A1 | 10/2013 | Matsuya et al. |
| 2014/0212894 A1 | 7/2014 | Endo et al. |

FOREIGN PATENT DOCUMENTS

| | | |
|---|---|---|
| CN | 101056989 A | 10/2007 |
| CN | 101374956 A | 2/2009 |
| CN | 103403549 A | 11/2013 |
| CN | 103733068 A | 4/2014 |
| EP | 1746104 A1 | 1/2007 |
| JP | 2003-107088 A | 4/2003 |
| JP | 2005-106694 | 4/2005 |

OTHER PUBLICATIONS

Shozushima, Sepsis 2011, 15 (Suppl. 3): P3.*
Shozushima et al. (J Infect Chemother, 2011, Vo.17. pp. 764-769.*
Semeraro et al. (Mediterranean Journal of Hematology and Infectious Diseases, 201, vol. 2, No. 3, pp. 1-18).*
Gude, "Biomarkers in sepsis: A comprehensive review," Journal of Clinical Cases and Investigations, Apr. 2012, vol. 4 (Issue 1), pp. 13-28.
Morange et al., "TLR4/Asp299Gly, CD14/C-206T, plasma levels of the soluble receptor CD14 and the risk of coronary heart disease: The PRIME Study," European Journal of Human Genetics, Dec. 2004, vol. 12(12), pp. 1041-1049.
Okamura et al., "Development of a point-of-care assay system for measurement of presepsin (sCD14-ST)," Clinica Chimica Acta, Jul. 2011, vol. 412(23), pp. 2157-2161.
Shozushima et al., "Usefulness of presepsin (sCD14-ST) measurements as a marker for the diagnosis and severity of sepsis that satisfied diagnostic criteria of systemic inflammatory response syndrome," Journal of Infection and Chemotherapy, Dec. 2011, vol. 17(6), pp. 764-769.
Extended European Search Report, dated Sep. 10, 2015, EP Application No. 13787336.0, 7 pages.
Rienk Nieuwland, et al., Cellular origin and procoagulant properties of microparticles in meningococcal sepsis; Hemostatis, Thrombosis, and Vascular Biology; Feb. 1, 2000; vol. 95, No. 3; The Netherlands.
Sang Mee Hwang, et al.; Thrombomodulin phenotype of a distinct monocyte subtype is an independent prognostic marker for disseminated intravascular coagulation; Critical Care; 2011, vol. 15, issue 2, R113.
Hideo Wada et al.; Igaku no Ayumi (Journal of Clinical and Experimental Medicine) 2011; 238(1): 63-68.
Yutaka Eguchi; Igaku no Ayumi (Journal of Clinical and Experimental Medicine) 2011; 238(1): 114-119.
Yasunori Yaegashi, et al.; Evaluation of a newly identified soluble CD14 subtype as a marker for sepsis; J. Infect Chemother; 2005, 11:234-238.
Gaku Takahashi, et al.; Severity assessment of sepsis by determination of the soluble CD14 subtype using the POC test; Medical Postgraduates; 2010, vol. 48, No. 1; 25-27.
Therapeutic Research; 2004; vol. 25, No. 8. 1689-1694.
International Search Report of PCT/JP2013/059486, dated May 21, 2013.

* cited by examiner

*Primary Examiner* — Lisa Cook
(74) *Attorney, Agent, or Firm* — Kilpatrick Townsend & Stockton LLP

(57) ABSTRACT

Markers useful in diagnosing disseminated intravascular coagulation (DIC) or infectious DIC are provided. In a method for detecting DIC of the present invention, sCD14-ST in a sample is measured. In a method of detecting infectious DIC of the present invention, sCD14-ST and a coagulation-related marker in a sample are measured.

8 Claims, 19 Drawing Sheets

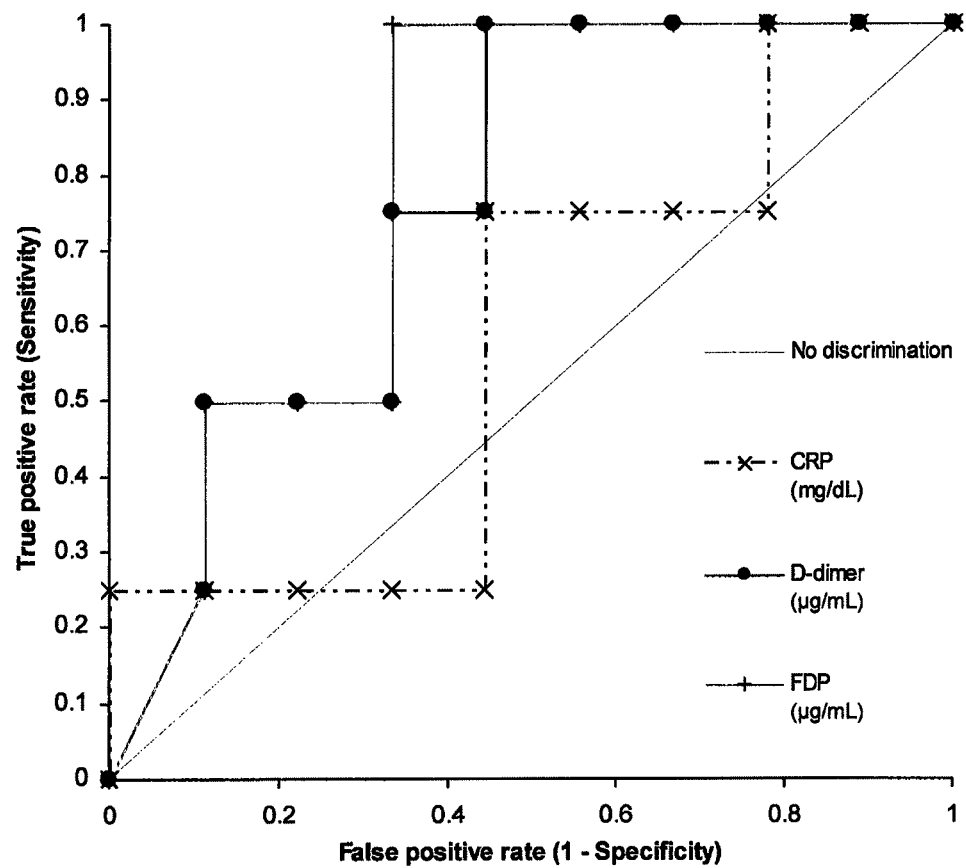

METHOD OF DIAGNOSING AND TREATING INFECTIOUS DISSEMINATED INTRAVASCULAR COAGULATION

CROSS-REFERENCE TO RELATED APPLICATIONS

This application is a national phase application under 35 U.S.C. 371 claiming priority to PCT/JP2013/062352, filed Apr. 26, 2013, which application claims priority to JP 2012-106216, filed May 7, 2012 and JP 2012-106217, filed May 7, 2012, the teachings of which are hereby incorporated by reference in their entireties for all purposes.

TECHNICAL FIELD

The present invention relates to a method of detecting disseminated intravascular coagulation (DIC), and a kit for carrying out said method. Further, the present invention relates to a method of detecting infectious disseminated intravascular coagulation (infectious DIC), and a kit for carrying out said method.

BACKGROUND ART

Disseminated intravascular coagulation (DIC) is a syndrome with an extremely high mortality rate, characterized by a tendency for bleeding due to consumption coagulopathy, and organ failure due to microvascular thrombosis, and rapid diagnosis and early treatment are necessary to maintain the life of patients and improve the prognosis. Conventional diagnosis of DIC in clinical practice includes the Japanese Ministry of Health and Welfare DIC diagnostic criteria, the measurements of various coagulation and fibrinolysis molecular markers [for example, soluble fibrin monomer (SF), D-dimer (DD), thrombin-antithrombin III complex (TAT), and α2-plasmin inhibitor/plasmin complex (PIC)], and the like. In addition, the International Society on Thrombosis and Haemostasis (ISTH) overt-DIC diagnostic criteria as a modification of the Japanese Ministry of Health and Welfare DIC diagnostic criteria, and the diagnostic criteria for the Japanese Association for Acute Medicine (JAAM) DIC are known. However, it is known that the Japanese Ministry of Health and Welfare DIC diagnostic criteria, and the ISTH overt-DIC diagnostic criteria exhibit low sensitivity, and the diagnostic criteria for JAAM DIC exhibits low specificity. Therefore, a study for diagnosis with high accuracy has been carried out (Non-patent literature 1) and, for example, the discovery of a marker with high sensitivity and high specificity is desired.

DIC is complicated with serious underlying diseases, such as malignant tumors, leukemia, or severe infections (or severe sepsis), and in particular, about 35% of patients suffering from severe sepsis are complicated with DIC. Since the mortality rate of patients complicated with DIC is increased from 22.2-26.5% to 40-46.2% in comparison with that of non-DIC, the diagnosis of septic DIC is very important to improve the prognosis of sepsis.

Because an underlying disease always exists in a DIC patient, the treatment for the underlying disease is first carried out. For example, chemotherapy for acute leukemia or advanced cancer, an antibiotic treatment sensitive to sepsis, or the like, is carried out. Because the underlying disease is diverse, it is important to grasp the patient's condition in order to select the most effective treatment. Even if a patient is diagnosed with DIC, it is needless to say that a wrong treatment would result in a serious condition.

With respect to septic DIC, it was reported that patients resistant to a treatment based on an antithrombin preparation could be effectively treated using a recombinant thrombomodulin preparation with an anti-inflammatory effect, in addition to an anticoagulant effect (Non-patent literature 2).

Conventionally, septic DIC is diagnosed by the judgment of a doctor, on the basis of the diagnostic criteria for sepsis or DIC. For example, as described above, for the diagnosis of DIC, in addition to the Japanese Ministry of Health and Welfare DIC diagnostic criteria, various coagulation and fibrinolysis molecular markers [for example, soluble fibrin monomer (SF), D-dimer (DD), thrombin-antithrombin III complex (TAT), and α2-plasmin inhibitor/plasmin complex (PIC)] are measured in clinical practice. In addition, the ISTH overt-DIC diagnostic criteria as a modification of the Japanese Ministry of Health and Welfare DIC diagnostic criteria, and the diagnostic criteria for JAAM DIC are known. However, it is known that the Japanese Ministry of Health and Welfare DIC diagnostic criteria, and the ISTH overt-DIC diagnostic criteria exhibit low sensitivity, and the diagnostic criteria for JAAM DIC exhibit low specificity.

On the other hand, for the diagnosis of sepsis, blood culture, white blood cell count, body temperature, diagnostic imaging, the duration of systemic inflammatory response syndrome (SIRS), blood biochemical findings, and the like, are used as an index. Further, procalcitonin (PCT) and sCD14-ST were reported as markers capable of conveniently detecting sepsis.

It is disclosed that the sCD14-ST value in a sample collected from a sepsis patient is much higher than that of healthy persons, and sepsis is diagnosed by measuring sCD14-ST (Non-patent literature 3 and Patent literature 1). It is disclosed that sCD14-ST is measured using an antibody specific to sCD14-ST (Patent literature 1 and Patent literature 2). A method of rapidly detecting sCD14-ST and a method of evaluating the severity thereof are disclosed (Patent literature 2 and Non-patent literatures 3-5). As described above, it is known that sCD14-ST can be used to accurately diagnose sepsis accompanied by bacterial infection, but it has not been reported that sCD14-ST is useful in the detection of DIC.

As described above, a marker capable of conveniently and accurately diagnosing septic DIC (or infectious DIC) has not been reported, and the fact is that doctors are struggling to diagnose septic DIC (or infectious DIC), and the discovery of such a marker is desired.

CITATION LIST

Patent Literature

[Patent literature 1] Japanese Patent No. 4040666
[Patent literature 2] Japanese Unexamined Patent Publication (Kokai) No. 2005-106694

Non-Patent Literature

[Non-patent literature 1] Igaku no Ayumi (Journal of Clinical and Experimental Medicine) 2011; 238(1): 63-68.
[Non-patent literature 2] Igaku no Ayumi (Journal of Clinical and Experimental Medicine) 2011; 238(1): 114-119.
[Non-patent literature 3] J Infect Chemother 2005; 11:234-238.
[Non-patent literature 4] Medical Postgraduates 2010; 48: 25-27.

[Non-patent literature 5] Therapeutic Research 2004; 25: 1689-1694.

SUMMARY OF INVENTION

Technical Problem

An object of the present invention is to provide a marker effective in diagnosing disseminated intravascular coagulation (DIC) or infectious DIC. After infectious DIC is suspected, there is a need to quickly determine an appropriate course of treatment therefor.

Solution to Problem

The present inventor conducted intensive study to solve the object, and examined the relationship between the amount of sCD14-ST in the blood and disseminated intravascular coagulation (DIC) in clinical trials. The inventor found that sCD14-ST was a specific marker which specifically reacts in a DIC patient with high sensitivity and specificity, and that DIC could be detected on the basis of the measured value or degree of sCD14-ST, and then completed the present invention. In particular, it was a surprising finding that DIC could be detected regardless of the presence or absence of infection.

Further, the inventor found that when infectious disseminated intravascular coagulation (infectious DIC) was suspected, the infectious DIC could be conveniently detected and the clinical condition could be understood, by measuring sCD14-ST and a coagulation-related marker contained in a sample, and based on the measured value or degree, and they were specific markers, and then the inventor completed the present invention.

The present invention relates to

[1] a method of detecting disseminated intravascular coagulation, comprising measuring sCD14-ST in a sample,

[2] the method of detecting disseminated intravascular coagulation of [1], comprising the steps of:

measuring sCD14-ST in a sample collected from a patient suspected of having disseminated intravascular coagulation, or a patient suffering from disseminated intravascular coagulation, and judging that the patient suffers from disseminated intravascular coagulation when an sCD14-ST value is higher than that of a non-disseminated-intravascular-coagulation patient,

[3] the method of [2], wherein the sCD14-ST value is compared in the judgment step to a threshold previously determined,

[4] the method of any one of [1] to [3], wherein sCD14-ST is measured by an immunoassay,

[5] the method of [1], comprising measuring a coagulation-related marker in a sample in addition to sCD14-ST, wherein disseminated intravascular coagulation is infectious disseminated intravascular coagulation,

[6] the method of [5], comprising the steps of:

measuring sCD14-ST and a coagulation-related marker in a sample collected from a patient suspected of having infectious disseminated intravascular coagulation, or a patient suffering from infectious disseminated intravascular coagulation, and judging that the patient suffers from infectious disseminated intravascular coagulation when an sCD14-ST value and a coagulation-related marker value are changed in comparison with those of a non-infectious-disseminated-intravascular-coagulation patient,

[7] the method of [6], wherein the sCD14-ST value and the coagulation-related marker value are compared in the judgment step to thresholds previously determined, respectively,

[8] the method of any one of [5] to [7], wherein the coagulation-related marker is at least one selected from the group consisting of D-dimer, FDP, thrombin-antithrombin III complex, platelet counts, and protein C,

[9] the method of any one of [5] to [8], wherein sCD14-ST is measured by an immunoassay,

[10] a kit for detecting disseminated intravascular coagulation, comprising:

(a) an antibody specific to sCD14-ST, (b) standard data showing a correlation between the amount of sCD14-ST in a sample and disseminated intravascular coagulation, and (c) an instruction manual,

[11] a kit for detecting infectious disseminated intravascular coagulation, comprising:

(a) an antibody specific to sCD14-ST, (b) a reagent for measuring a coagulation-related marker, (c) standard data showing a correlation between measured values of sCD14-ST and the coagulation-related marker in a sample and infectious disseminated intravascular coagulation, and (d) an instruction manual, and

[12] the kit of [11], wherein the coagulation-related marker is at least one selected from the group consisting of D-dimer, FDP, thrombin-antithrombin III complex, platelet counts, and protein C.

The term "human sCD14-ST" (also referred to as Presepsin (registered trademark)) as used herein means the "soluble CD14 antigen of the first aspect" disclosed in Japanese Patent No. 4040666 and, more particularly, is a soluble CD14 antigen with the following characteristics 1) to 3):

1) Having a molecular weight of 13±2 kDa as measured by SDS-PAGE under non-reducing conditions;

2) Having the amino acid sequence of SEQ ID NO: 1 at the N-terminal sequence; and 3) Binding specifically to an antibody prepared by using a peptide consisting of 16 amino acid residues of SEQ ID NO: 2 as an antigen.

```
SEQ ID NO: 1:
Thr Thr Pro Glu Pro Cys Glu Leu Asp Asp Glu
1               5                   10

SEQ ID NO: 2:
Arg Val Asp Ala Asp Ala Asp Pro Arg Gln Tyr
1               5                   10

Ala Asp Thr Val Lys
            15
```

The term "infection" as used herein includes infection by bacteria, fungi, parasites, viruses, or the like.

The method for confirming the presence of infection is not particularly limited, but examples thereof include, in addition to a commonly-used blood culture, gene identification methods (such as PCR and RP-PCR), diagnostic imaging, ultrasonic diagnosis, endoscopy, and biopsy (Am. J. Infect. Control, 1988; 16: 128-140).

The term "infection (as infectious diseases)" as used herein means a phenomenon characterized by the invasion of normal tissues by microorganisms, or the inflammatory response to the presence of the microorganisms (Chest 1992; 101(6): 1644-1655). Pathogens that cause infections include bacteria, fungi, parasites, and viruses. Bacteremia, sepsis, severe sepsis, and septic shock are included among said "infections". Bacteremia is a state in which viable bacteria are present in the blood (Saishin Naika-gaku Taikei (Integrated Handbook of Internal Medicine), Vol. 27, Saikin Kansen-sho (Bacterial Infections), 1994: 69-84). Sepsis is a systemic inflammatory response syndrome (SIRS) caused by infection, and a state in which microorganisms such as bacteria or fungi and their metabolites are continuously migrating from the focus of infection in the body into the blood.

The term "sepsis" as used herein means a systemic inflammatory response syndrome (SIRS) which is caused by infection. That is to say, sepsis is a very severe state in which the infection has spread throughout the body, and some of the patients without treatment die due to shock, DIC, multiple organ failure, or the like. "Sepsis" means a state wherein a patient satisfies, in addition to the presence of the above-mentioned infection, for example, two or more criteria out of the following four criteria, which are the criteria for the diagnosis of systemic inflammatory response syndrome (SIRS) (Chest, 1992; 101 (6): 1644-1655):

1) Body temperature >38° C. or <36° C.;
2) Heart rate >90 per minute;
3) Respiration rate >20 per minute or $PaCO_2$>32 Torr; and
4) White blood cell count >12000 or <4000/mm$^3$, or immature leukocytes >10%.

The term "infectious DIC" as used herein means disseminated intravascular coagulation (DIC) with an infection (or sepsis) as an underlying disease. For example, it is said that about 35% of patients suffering from severe sepsis have DIC complications. Conventionally, "infectious DIC" (or "septic DIC") is diagnosed by the comprehensive judgment of a doctor, on the basis of the diagnostic criteria for infection (or sepsis) and the diagnostic criteria for DIC, and the clinical condition is grasped.

Its treatment is a symptomatic treatment of pathological conditions. For example, an antibacterial agent or the like, and an anticoagulant or the like are appropriately used for the treatments of infection (or sepsis) and DIC, respectively.

Advantageous Effects of Invention

According to the method of the present invention, the onset of disseminated intravascular coagulation (DIC) or infectious DIC can be detected rapidly and accurately, and thus, an appropriate course of treatment can be determined.

The kit of the present invention can be used in the method of the present invention.

BRIEF DESCRIPTION OF THE DRAWINGS

FIG. 37 is a graph showing the results of ROC analysis. With respect to the patients classified in a similar fashion to those in FIG. 36, each usefulness for DIC detection of C-reactive protein (CRP), D-dimer, and fibrin/fibrinogen degradation products (FDP) in samples collected on admission was compared to one another by ROC analysis.

DESCRIPTION OF EMBODIMENTS

Figure 1:
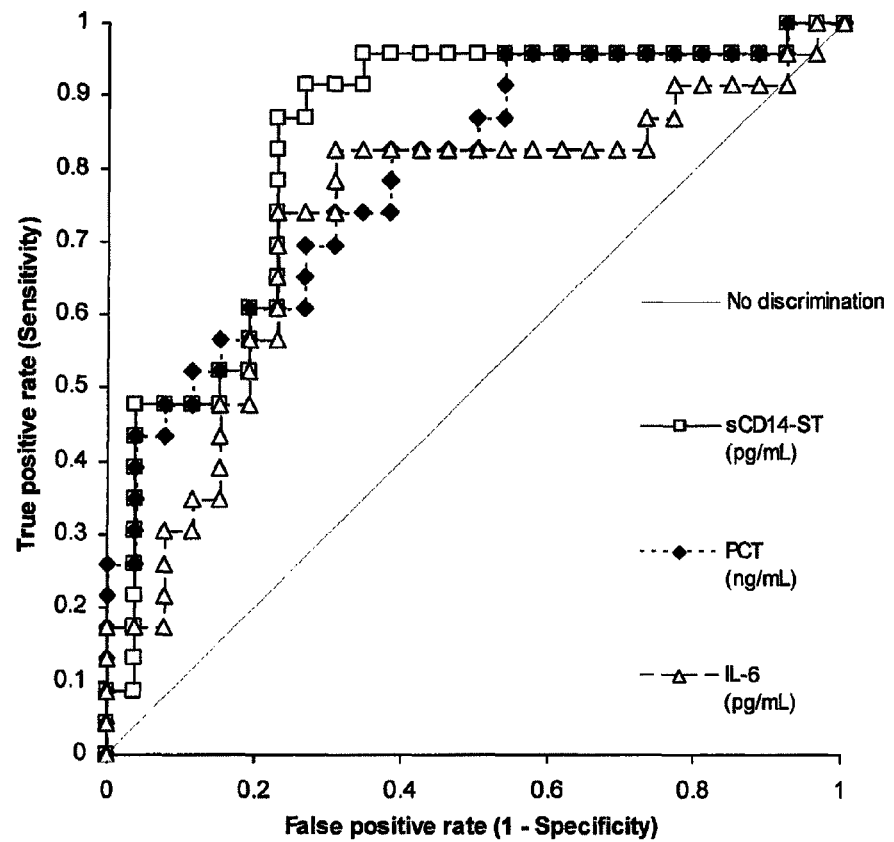
FIG. 1 is a graph showing the results of ROC analysis. Patients (49 cases) registered in a clinical study were classified into a DIC group (23 cases) and a non-DIC group (26 cases) on the basis of the diagnostic criteria for JAAM DIC, and each usefulness for DIC detection of sCD14-ST, procalcitonin (PCT), and interleukin-6 (IL-6) in samples collected on admission was compared to one another by ROC analysis.

In the detection method of the present invention (hereinafter referred to as the method of the present invention), sCD14-ST in a sample collected from a subject, in particular, a patient suspected of having disseminated intravascular coagulation (DIC) or a patient suffering from DIC, is measured. Further, in the case of detecting infectious DIC in the method of the present invention, sCD14-ST and a coagulation-related marker in a sample collected from a patient suspected of having infectious disseminated intravascular coagulation (infectious DIC) or a patient suffering from infectious DIC, are measured.

Examples of the coagulation-related marker which may be used in the present invention include D-dimer, fibrin/fibrinogen degradation products (FDP), platelet counts (Plt), prothrombin time (PT), INR value, activated partial thromboplastin time (APTT), fibrinogen (FIB), antithrombin III (ATIII)(quantitation, activity), lactate (Lact), thrombin-antithrombin complex (TAT), α2-plasmin inhibitor/plasmin complex (PIC), protein C (PC) (quantitation, activity), thrombomodulin (TM), tissue plasminogen activator (tPA)/plasminogen activator inhibitor (PAI-1) complex (Total PAI-1), plasminogen activator inhibitor (PAI-1), soluble fibrin (SF), E-selectin, and the like; and preferably D-dimer, FDP, TAT, platelet counts, and PC.

Methods of measuring sCD14-ST and each coagulation-related marker are known, and commercially available assay reagents or measuring apparatuses may be used. As various known analytical methods for proteins, for example, an immunoassay using an antibody, or a biochemical assay such as electrophoresis may be carried out, and an autoanalyzer for a clinical laboratory test may also be used. Analytical methods that use a substance with similar properties to those of an antibody, such as an RNA aptamer, are included in the present invention.

For example, Japanese Patent No. 4040666 discloses a method for measuring human sCD14-ST, more particularly, sandwich EIA systems using combinations of a polyclonal antibody (S68 antibody) or a monoclonal antibody (F1146-17-2 antibody), which were prepared using a peptide consisting of 16 amino acid residues of SEQ ID NO: 2 (the S68 peptide described in Japanese Patent No. 4040666) as an antigen, and anti-CD14-antigen monoclonal antibodies (for example, F1031-8-3 antibody, F1106-13-3 antibody, or the like) [Example 7-(1) in Japanese Patent No. 4040666], and these can be applied to the method of the present invention.

Further, as shown in the Examples described below, sCD14-ST can be measured using an automated chemiluminescent immunoassay analyzer (PATHFAST; manufactured by LSI Medience Corporation) by a chemiluminescent enzyme immunoassay using magnetic particles.

A sample used in the method of the present invention is not particularly limited, so long as sCD14-ST (and a coagulation-related marker, if desired) can be measured. For example, blood samples (such as whole blood, plasma, or serum) may be used. The skilled artisan can select and use an appropriate sample.

In the method of the present invention, an increase in the sCD14-ST concentration in a sample is used as an index of DIC. For example, as shown in the Examples described below, the sCD14-ST value significantly increases in a DIC patient. More particularly, as shown in Examples 5 and 8, the cutoff value (threshold value) of sCD14-ST exhibits a high value, such as 1100 pg/mL, and this can be used to judge DIC with high sensitivity and specificity. As described above, in the method of the present invention, when the sCD14-ST value shows a high value, it can be judged that DIC occurs. By contrast, when the sCD14-ST value shows a low value, it can be judged that DIC does not occur. For example, when the sCD14-ST concentration in a sample is higher than a quantile value (for example, median) of healthy persons or non-DIC patients, it can be judged that DIC occurs. Further, the judgment may be carried out by statistical techniques such as a Cox regression or a logistic regression. As the criteria for judgment, a "threshold value" determined in advance can be used.

In the method of the present invention, although the threshold value for the sCD14-ST concentration in order to detect DIC is expected to vary according to various conditions, such as sex or age, the threshold value for the judgment can be determined for those skilled in the art by appropriately selecting a suitable population that corresponds to the subjects, and statistically process the data acquired from the population. As for the population, a healthy person group, a non-DIC group, DIC groups of different pathological types, or the like, can be selected. In Example 5 described below, an optimal cutoff value of 1100 pg/mL has been determined on the basis of ROC analysis of the non-DIC group and the DIC group. In the method of the present invention, it is possible to automatically detect DIC, without requiring judgment of a doctor, by determining the threshold value for the judgment, and comparing the measured sCD14-ST concentration in a sample with the threshold value for said judgment.

It is preferable that the cutoff value for detecting DIC is appropriately set on the basis of the distribution of a DIC group and a non-DIC group. More particularly, the cutoff value for detecting DIC is 150 to 10000 pg/mL, preferably 250 to 5000 pg/mL, and more preferably 500 to 2300 pg/mL. The skilled artisan can appropriately set the single cutoff value in this range without undue trial and error.

In the method of the present invention, an increase or decrease in the sCD14-ST value and the coagulation-related marker value in a sample is used as an index of infectious DIC. For example, as shown in Examples 11 and 14 described below, when infectious DIC occurs, the values of sCD14-ST, D-dimer, fibrin/fibrinogen degradation products (FDP), prothrombin time (PT (sec.)), INR, lactate, thrombin-antithrombin complex (TAT), α2-plasmin inhibitor/plasmin complex (PIC), thrombomodulin (TM), and tissue plasminogen activator (tPA)/plasminogen activator inhibitor (PAI-1) complex (Total PAI-1) increase, but the values of platelet (Plt) counts, PT (%), activated partial thromboplastin time (APTT), fibrinogen (FIB), antithrombin III (ATIII) (%), and protein C (PC)(%) decrease. In particular, the combination of sCD14-ST with the coagulation-related marker is preferable as the index, and more preferably, sCD14-ST can be used by combining it with at least one selected from D-dimer, FDP, TAT, platelet counts, and PC. Further, a plurality of sepsis markers or coagulation-related markers can be used as a combination thereof.

For example, when sCD14-ST shows a high value, and D-dimer, FDP, or TAT shows a high value, or platelet counts or PC shows a low value, it can be judged that infectious DIC occurs. When sCD14-ST shows a low value, or D-dimer, FDP, or TAT shows a low value, or platelet or PC shows a high value, it can be judged that infectious DIC does not occur. Such a high value or low value may be shown by comparing each value with a quantile value (for example, median) of healthy persons, infectious non-DIC patients, or the like. The comparison may be carried out by statistical techniques such as a Cox regression or a logistic regression. As the criteria for judgment, a "threshold value" determined in advance can be used.

In the method of the present invention, although the threshold value for the sCD14-ST concentration and the measured value of a coagulation-related marker in order to detect infectious DIC is expected to vary according to various conditions, such as sex or age, the threshold value for the judgment can be determined for those skilled in the art by appropriately selecting a suitable population that corresponds to the subjects, and statistically process the data acquired from the population. As for the population, a healthy person group, a DIC group, a non-DIC group, a non-infection group, an infection group, a SIRS group, a sepsis group, a severe sepsis group, a septic shock group, septic groups of different pathological severity level, septic groups of different pathological types, an infectious DIC group, an infectious non-DIC group, or the like, can be selected. With respect to the sCD14-ST value, as shown in Example 13 described below, an optimal cutoff value of 900 to 1000 μg/mL has been determined. As shown in Example 15, with respect to the D-dimer value, FDP value, TAT value, and platelet counts, optimal cutoff values of 6.18 μg/mL or 10 μg/mL, 25 μg/mL or 35 μg/mL, 10 ng/mL or 26 ng/mL, and $12\times10^4$ cells/μL have been determined, respectively. As shown in Example 20, with respect to the PC value, an optimal cutoff value of 45% or 55% has been determined. In the method of the present invention, it is possible to automatically detect infectious DIC, without requiring a doctor's judgment, by determining the threshold value for the judgment, and comparing the measured sCD14-ST concentration and the measured value of a coagulation-related marker in a sample with the threshold value for the judgment.

It is preferable that the cutoff value for detecting infectious DIC is appropriately set on the basis of the distribution of an infectious DIC group and an infectious non-DIC group. For example, the cutoff value of sCD14-ST is 150 to 10000 pg/mL, preferably 250 to 5000 pg/mL, and more preferably 500 to 2300 pg/mL. The skilled artisan can appropriately set the single cutoff value in this range without undue trial and error.

In the method of the present invention, the time for sample collection is preferably at a stage where suspicion of DIC or infectious DIC has been raised, or a stage after the treatment. A change in clinical condition can be appropriately grasped by collecting samples over time and carrying out the measurement.

The kit of the present invention for detecting DIC can be used for carrying out the method of the present invention and includes:
(a) an antibody specific to sCD14-ST;
(b) standard data showing a correlation between the amount of sCD14-ST in a sample and DIC; and
(c) an instruction manual.

The kit of the present invention for detecting infectious DIC can be used for carrying out the method of the present invention and includes:
(a) an antibody specific to sCD14-ST;
(b) a reagent for measuring a coagulation-related marker,
(c) standard data showing a correlation between measured values of sCD14-ST and the coagulation-related marker in a sample and infectious DIC, and
(d) an instruction manual.

The antibody used in the kit of the present invention may be a monoclonal antibody or a polyclonal antibody. Further, an antibody fragment that retains a specific binding activity to sCD14-ST, for example, Fab, Fab', F(ab')$_2$, or Fv, may be used in the kit.

Further, the antibody can be used, as it is, in the kit, or can be used in the kit in a suitable form based on the immunological technique to be employed, for example, by being immobilized onto a latex carrier when employing a latex agglutination immunoassay, by being immobilized onto magnetic particles when employing a highly sensitive measuring method using magnetic particles, or the like, by being immobilized onto a substrate when employing a method that uses a substrate, such as an immunochromatography, or by being labeled with labeling substances (for example, enzymes, fluorescent substances, chemiluminescent substances, radioactive isotopes, biotin, or avidin) if necessary.

The reagent for measuring a coagulation-related marker, which may be used in the kit of the present invention, may be provided by appropriately combining known reagents with one another.

The standard data included in the kit of the present invention for detecting DIC are not particularly limited, so long as they show a correlation between the amount of sCD14-ST in a sample and DIC, and examples thereof include a threshold value for the judgment, and original data or statistically processed data for calculating the threshold value for the judgment. The standard data included in the kit of the present invention for detecting infectious DIC are not particularly limited, so long as they show a correlation between measured values of sCD14-ST and the coagulation-related marker in a sample and infectious DIC, and examples thereof include a threshold value for the judgment, and original data or statistically processed data for calculating the threshold value for the judgment. The standard data may be described in the instruction manual, or may be attached separately as a data sheet. Further, the form of the attached document includes paper, electronic media such as CD-ROM, and those downloaded from homepages or the like.

The instruction manual included in the kit of the present invention for detecting DIC is not particularly limited, so long as it refers at least to the relationship between the amount of sCD14-ST in a sample and DIC. In addition to the above reference, the instruction manual can include, for example, an explanation regarding the procedure for carrying out an immunological measurement using the kit of the present invention, an explanation regarding the procedure for detecting DIC based on the obtained measured values, precautions regarding the storage and handling of the kit per se, or the like. The instruction manual included in the kit of the present invention for detecting infectious DIC is not particularly limited, so long as it refers at least to the relationship between the measured values of sCD14-ST and a coagulation-related marker in a sample and infectious DIC. In addition to the above reference, the instruction manual can include, for example, an explanation regarding the procedure for carrying out an immunological measurement using the kit of the present invention, an explanation regarding the procedure for detecting infectious DIC based on the obtained measured values, precautions regarding the storage and handling of the kit per se, or the like.

EXAMPLES

The present invention now will be further illustrated by, but is by no means limited to, the following Examples.
<<Subjects to be Tested 1>>

The subjects to be tested in Examples 1 to 15, Comparative Example 1, and Referential Example 1 were as follows.

Emergency patients who had been registered for a certain period of time in a single facility for clinical practice were tested. This study was approved by the ethics committee. The patients registered in this study were men and women at least 18 years old who were admitted to an emergency hospital, and met at least one item among the following four items:
1) Body temperature >38° C. or <36° C.;
2) Heart rate >90 per minute;
3) Respiration rate >20 per minute or $PaCO_2$>32 Torr; and
4) White blood cell count >12000 or <4000/mm$^3$, or immature leukocytes >10%.

The cases registered in this study were 49 cases, and were classified into a DIC patient group and a non-DIC patient group, on the basis of each diagnostic criteria for DIC, as described in Examples below.

Further, separately, the presence or absence of underlying diseases was classified as follows. Systemic inflammatory response syndrome (SIRS) without infection was 9 cases, sepsis was 6 cases, severe sepsis was 12 cases, septic shock was 10 cases, noninfectious diseases (a state of neither infection nor SIRS) were 4 cases, and infectious diseases (a state of infection without SIRS) were 8 cases.

The judgment of DIC in each patient was carried out on the basis of three diagnostic criteria for DIC, i.e., the diagnostic criteria for JAAM DIC, the Japanese Ministry of Health and Welfare DIC diagnostic criteria, and the ISTH overt-DIC diagnostic criteria. The definition of each diagnostic criteria will be explained hereafter.

TABLE 1

Diagnostic criteria for JAAM DIC

| Score | SIRS | Platelet (mm$^3$) | PT ratio | FDP (μg/mL) |
|---|---|---|---|---|
| 0 | 0-2 | 120,000≤ | <1.2 | <10 |
| 1 | ≥3 items, positive | 80,000≤ or <120,000 or decrease by ≥30% in 24 hr. | 1.2≤ | 10≤ or <25 |
| 2 | — | — | — | — |
| 3 | — | <80,000 or decrease by ≥50% in 24 hr. | | 25≤ |
| | | ≥4 points are judged as DIC | | |

Notes:
1) Decrease in platelet counts can be determined within 24 hours before or after the score calculation.
2) Prothrombin time (PT) ratio (PT sec. of sample/normal control value) when ISI = 1.0, equals to INR. In each facility, decrease of activity value or extension of the numbers of seconds corresponding to the PT ratio 1.2 may be used.
3) Instead of fibrin/fibrinogen degradation products (FDP), D-dimer may be used. In accordance with a measuring kit used in each facility, a conversion table in Annex is used.

TABLE 2

Japanese Ministry of Health and Welfare DIC diagnostic criteria

| | Hematopoietic organ tumor (+) | Hematopoietic organ tumor (−) |
|---|---|---|
| Underlying disease Clinical symptom | Underlying disease: 1 point (presence) Organ symptom: 1 point (presence) | Underlying disease: 1 point (presence) Bleeding symptom: 1 point (presence) Organ symptom: 1 point (presence) |
| Platelet (×10$^3$/μL) | | 80-120: 1 point 50-80: 2 points 50>: 3 points |
| Serum FDP (μg/mL) | 10-20: 1 point 20-40: 2 points 40<: 3 points | |
| Fibrinogen (FIB) | 100-150 mg/dL: 1 point 100 mg/dL>: 2 points | |
| PT | PT ratio 1.25-1.67: 1 point 1.67<: 2 points | |
| DIC | ≥4 points | ≥7 points |

TABLE 3

ISTH overt-DIC diagnostic criteria

| Underlying disease | Essential item |
|---|---|
| Clinical symptom | Currently ignored |
| Platelet (×10$^3$/μL) | 50-100: 1 point 50>: 2 points |
| Fibrin-related product | FDP, D-dimer, SF: Moderate increase: 2 points Strong increase: 3 points |
| Fibrinogen (FIB) | 100 mg/dL>: 1 point |
| PT | PT sec: 3-6 sec prolongation: 1 point ≥6 sec prolongation: 2 points |
| DIC | ≥5 points |

The presence or absence of underlying diseases was classified on the basis of the following:

The disease "SIRS" means a state where a patient satisfies two or more items out of the following four items [Chest 1992; 101(6):1644-1655]:
1) Body temperature >38° C. or <36° C.;
2) Heart rate >90 per minute;
3) Respiration rate >20 per minute or $PaCO_2$>32 Torr; and
4) White blood cell count >12000 or <4000/mm$^3$, or immature leukocytes >10%.

"Infection" means a phenomenon characterized by the invasion of normal tissues by microorganisms, or the inflammatory response to the presence of the microorganisms (Chest 1992; 101(6):1644-1655). Pathogens that cause infections include bacteria, fungi, parasites, and viruses. Bacteremia, sepsis, severe sepsis, and septic shock are included in the "infections".

The disease "sepsis" means SIRS with infection. The diagnosis of infection needs inflammation findings, organ symptoms, and the identification of a pathogenic bacterium, and a diagnosis is confirmed by a doctor. For the identification of a pathogenic bacterium, it is preferable to aseptically collect blood, spinal fluid, chest ascites, or the like, and when sputum, urine, skin, or the like is used as a material, it is important to pay attention to indigenous bacteria. In the case where the identification of a pathogenic bacterium is not possible, the diagnosis of sepsis can be carried out by the comprehensive judgment of a doctor.

The disease "severe sepsis" means a state where a patient suffering from sepsis is complicated with organ dysfunction/circulatory failure (lactic acidosis, oliguria, acute disturbance of consciousness, or the like) or hypotension (systolic blood pressure: <90 mmHg, or decrease in blood pressure of 40 mmHg or more from the normal systolic blood pressure).

The disease "septic shock" means a state where hypotension (systolic blood pressure: <90 mmHg, or decrease in blood pressure of 40 mmHg or more from the normal systolic blood pressure) persists even after appropriate fluid replacement in severe sepsis. Even if blood pressure is maintained by a vasoactive drug, organ dysfunction/circulatory failure (lactic acidosis, oliguria, acute disturbance of consciousness, or the like) persist.

As samples used for the measurement of sCD14-ST, EDTA whole blood was collected from patients after admission by a conventional method, and sCD14-ST was measured. Similarly, EDTA plasma was collected for the measurements of procalcitonin (PCT), interleukin-6 (IL-6), and C-reactive protein (CRP); and citrated plasma was collected for the measurements of D-dimer, fibrin/fibrinogen degradation products (FDP), prothrombin time (PT), fibrinogen (FIB), activated partial thromboplastin time (APTT), antithrombin III (ATIII), thrombin-antithrombin complex (TAT), α2-plasmin inhibitor/plasmin complex (PIC), protein C (PC), and tissue plasminogen activator (tPA)/plasminogen activator inhibitor (PAI-1) complex (Total PAI-1). EDTA added blood, a deproteinized supernatant, and a serum were collected for the measurements of platelet counts (Plt), lactate (Lact), and thrombomodulin (TM), respectively. The term "after admission" means within 3 hours post-admission.

Example 1: Measurement of Sepsis Marker

The measurement of sCD14-ST was carried out by modifying the method described in Example 7-(1) of Japanese Patent No. 4040666. More particularly, a polyclonal antibody (S68 antibody) labeled with alkaline phosphatase (ALP) and a monoclonal antibody (F1031-8-3 antibody) immobilized on magnetic particles (manufactured by JSR) were used, and the measurement was carried out using an automated chemiluminescent enzyme immunoassay analyzer (PATHFAST; manufactured by LSI Medience Corporation). The polyclonal antibody (S68 antibody) labeled with alkaline phosphatase (ALP) was prepared by preparing a Fab' fraction of the polyclonal antibody (S68 antibody) and linking the same with ALP via a maleimide method. CPD-star (manufactured by Applied Biosystems) was used as the luminescent substrate.

The measurement was carried out as follows. A sample was reacted with the antibody immobilized on magnetic particles and the ALP-labeled antibody, to form a complex composed of sCD14-ST contained in the sample and both antibodies. The complex was collected by a magnetic body to remove the unbound ALP-labeled antibody from the reaction mixture. The luminescent substrate was added to detect the amount of the luminescence as the amount of sCD14-ST.

The measurement of procalcitonin (PCT) was carried out using ECLusys BRAHMS PCT (Roche Diagnostics).

Interleukin-6 (IL-6) was measured using Immulyze IL-6 (Siemens Healthcare Diagnostics, Inc.).

C-reactive protein (CRP) was measured using CRP-latex X2 "Seiken" (Denka Seiken Co., Ltd.). Hitachi 7170S (Hitachi High-Technologies Corporation) was used as the measuring apparatus.

Figure 2:
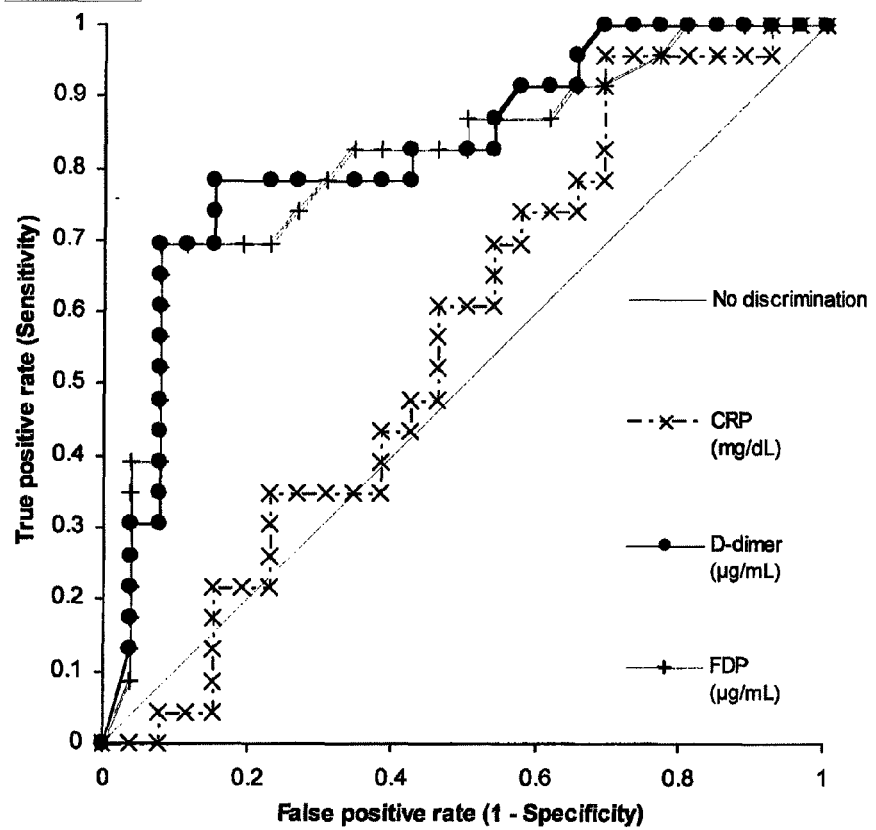
FIG. 2 is a graph showing the results of ROC analysis. With respect to the patients classified in a similar fashion to those in FIG. 1, each usefulness for DIC detection of C-reactive protein (CRP), D-dimer, and fibrin/fibrinogen degradation products (FDP) in samples collected on admission was compared to one another by ROC analysis.

Example 2: Evaluation of the Diagnostic Performance of Each Marker for DIC Based on the Diagnostic Criteria for JAAM DIC The 49 cases that had been registered in this clinical study were classified into a DIC group (23 cases) and a non-DIC group (26 cases), on the basis of the diagnostic criteria for JAAM DIC, and each usefulness of sCD14-ST, procalcitonin (PCT), C-reactive protein (CRP), interleukin-6 (IL-6), D-dimer, and fibrin/fibrinogen degradation products (FDP) for DIC detection was compared to one another by ROC analysis. The measurement of sCD14-ST was carried out in accordance with Example 1. The measurement of PCT was carried out using ECLusys BRAHMS PCT (Roche Diagnostics). Interleukin-6 (IL-6) was measured using Immulyze IL-6 (Siemens Healthcare Diagnostics, Inc.). CRP was measured using CRP-latex X2 "Seiken" (Denka Seiken Co., Ltd.). Hitachi 7170S (Hitachi High-Technologies Corporation) was used as the measuring apparatus. D-dimer was measured using Nanopia D-dimer (Sekisui Medical Co., Ltd.). Coapresta 2000 (Sekisui Medical Co., Ltd.) was used as the measuring apparatus. FDP was measured using Nanopia p-FDP (Sekisui Medical Co., Ltd.). Coapresta 2000 (Sekisui Medical Co., Ltd.) was used as the measuring apparatus. In FIGS. 1 and 2, the horizontal axis is the "1-specificity", and the vertical axis is "sensitivity".

The calculated AUCs were 0.834 (sCD14-ST), 0.791 (PCT), 0.734 (IL-6), 0.567 (CRP), 0.824 (D-dimer), and 0.810 (FDP), and the AUC of sCD14-ST was the highest. It was confirmed from this result that sCD14-ST was more useful than conventional markers, such as D-dimer, FDP, and the like.

Figure 3:
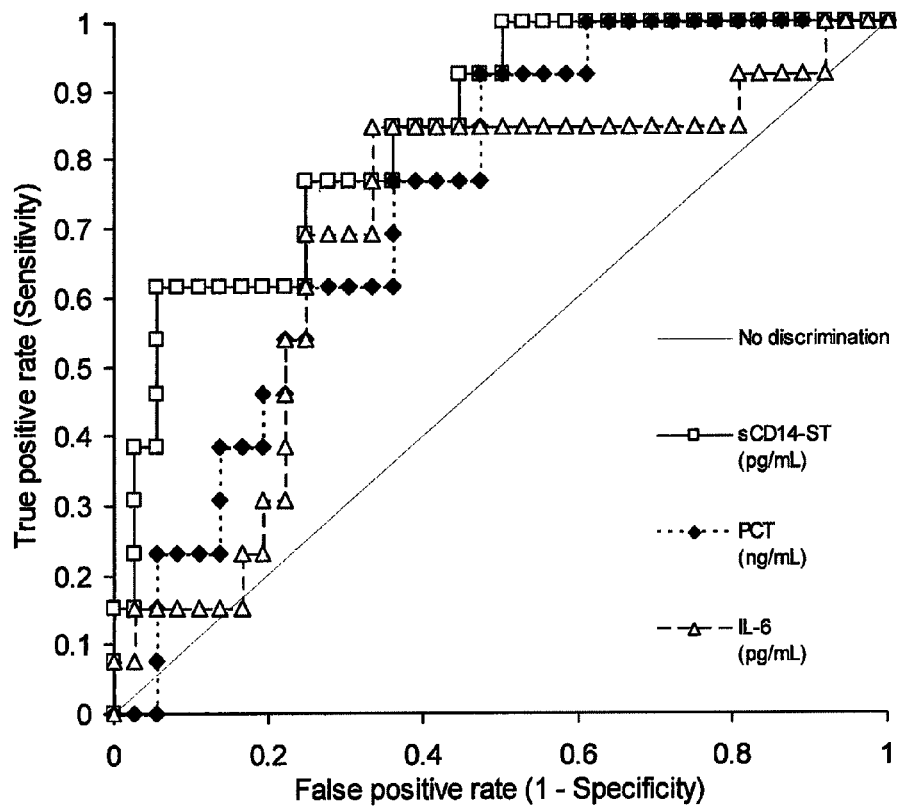
FIG. 3 is a graph showing the results of ROC analysis. Patients (49 cases) registered in a clinical study were classified into a DIC group (23 cases) and a non-DIC group (26 cases) on the basis of the Japanese Ministry of Health and Welfare DIC diagnostic criteria, and each usefulness for DIC detection of sCD14-ST, procalcitonin (PCT), and interleukin-6 (IL-6) in samples collected on admission was compared to one another by ROC analysis.
Figure 4:
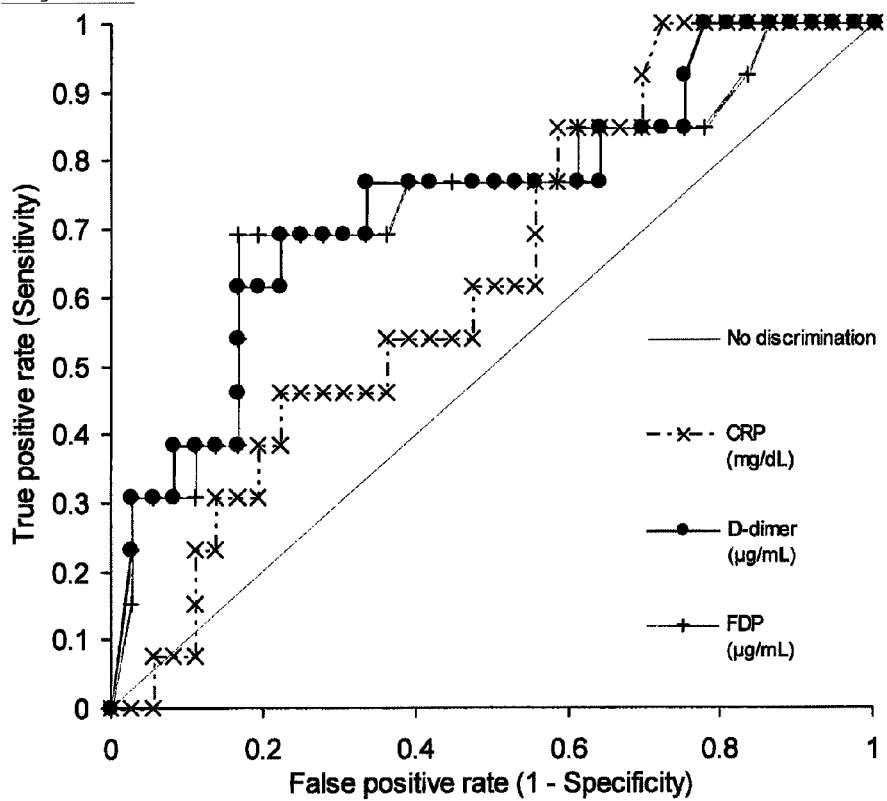
FIG. 4 is a graph showing the results of ROC analysis. With respect to the patients classified in a similar fashion to those in FIG. 3, each usefulness for DIC detection of C-reactive protein (CRP), D-dimer, and fibrin/fibrinogen degradation products (FDP) in samples collected on admission was compared to one another by ROC analysis.

Example 3: Evaluation of the Diagnostic Performance of Each Marker for DIC Based on the Japanese Ministry of Health and Welfare DIC Diagnostic Criteria The same 49 cases as those in Example 2 were classified into a DIC group (13 cases) and a non-DIC group (36 cases), on the basis of the Japanese Ministry of Health and Welfare DIC diagnostic criteria, and each usefulness of sCD14-ST, procalcitonin (PCT), C-reactive protein (CRP), interleukin-6 (IL-6), D-dimer, and fibrin/fibrinogen degradation products (FDP) for DIC detection was compared to one another by ROC analysis. The measurements of sCD14-ST, PCT, CRP, IL-6, D-dimer, and FDP were carried out by the same methods as those described in Example 2. In FIGS. 3 and 4, the horizontal axis is the "1-specificity", and the vertical axis is "sensitivity".

The calculated AUCs were 0.842 (sCD14-ST), 0.739 (PCT), 0.697 (IL-6), 0.634 (CRP), 0.741 (D-dimer), and 0.731 (FDP), and the AUC of sCD14-ST was the highest. It was confirmed from this result that sCD14-ST is more useful than conventional markers, such as D-dimer, FDP, and the like.

Figure 5:
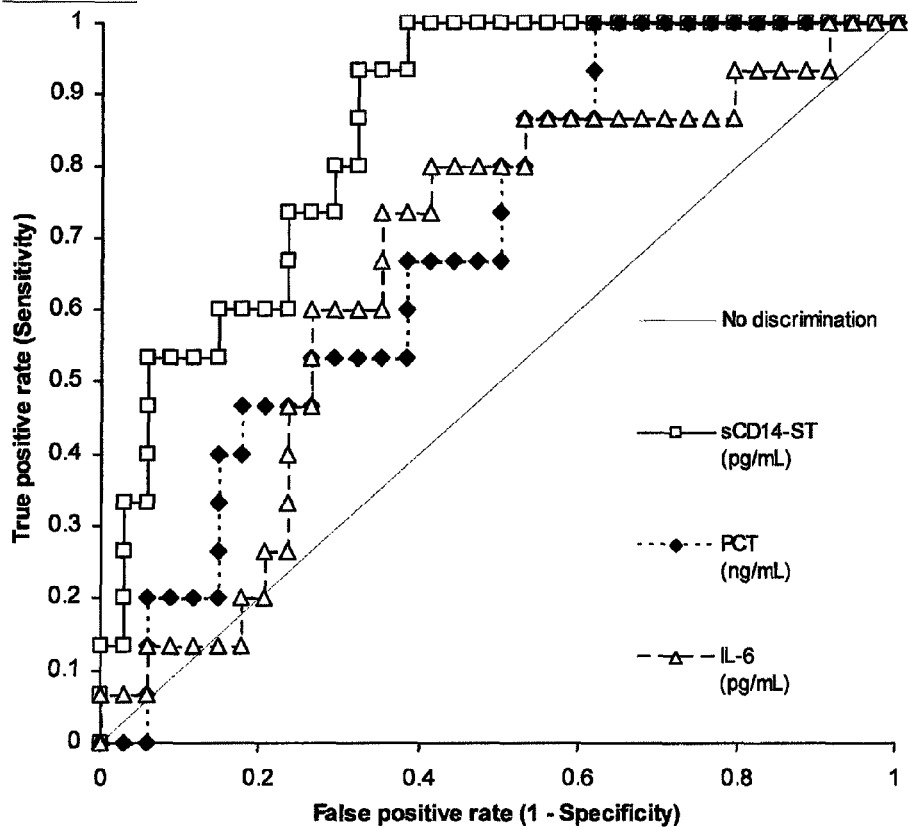
FIG. 5 is a graph showing the results of ROC analysis. Patients (49 cases) registered in a clinical study were classified into a DIC group (23 cases) and a non-DIC group (26 cases) on the basis of the ISTH overt-DIC diagnostic criteria, and each usefulness for DIC detection of sCD14-ST, procalcitonin (PCT), and interleukin-6 (IL-6) in samples collected on admission was compared to one another by ROC analysis.
Figure 6:
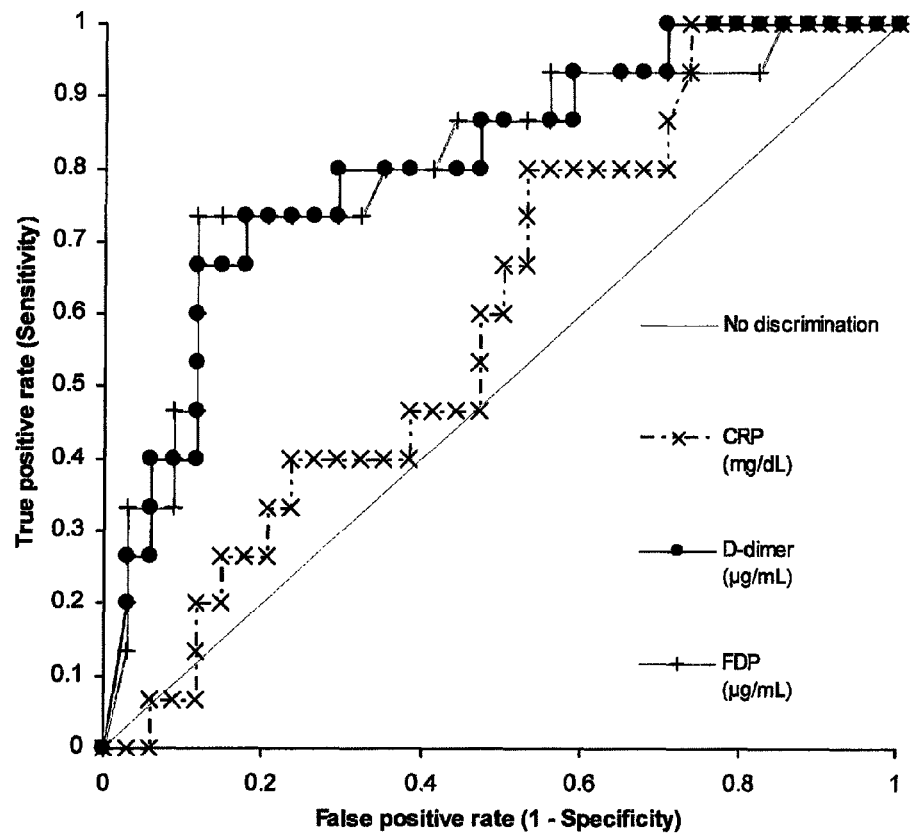
FIG. 6 is a graph showing the results of ROC analysis. With respect to the patients classified in a similar fashion to those in FIG. 5, each usefulness for DIC detection of C-reactive protein (CRP), D-dimer, and fibrin/fibrinogen degradation products (FDP) in samples collected on admission was compared to one another by ROC analysis.

Example 4: Evaluation of the Diagnostic Performance of Each Marker for DIC Based on the ISTH Overt-DIC Diagnostic Criteria The same 49 cases as those in Example 2 were classified into a DIC group (15 cases) and a non-DIC group (34 cases), on the basis of the ISTH overt-DIC diagnostic criteria, and each usefulness of sCD14-ST, procalcitonin (PCT), C-reactive protein (CRP), interleukin-6 (IL-6), D-dimer, and fibrin/fibrinogen degradation products (FDP) for DIC detection was compared to one another by ROC analysis. The results are shown in FIGS. 5 and 6. The measurements of sCD14-ST, PCT, CRP, IL-6, D-dimer, and FDP were carried out by the same methods as those described in Example 2. In FIGS. 5 and 6, the horizontal axis is the "1-specificity", and the vertical axis is "sensitivity".

The calculated AUCs were 0.853 (sCD14-ST), 0.694 (PCT), 0.665 (IL-6), 0.605 (CRP), 0.807 (D-dimer), and 0.805 (FDP), and the AUC of sCD14-ST was the highest. It was confirmed from this result that sCD14-ST is more useful than conventional markers, such as D-dimer, FDP, and the like.

Example 5: Evaluation of sCD14-ST Cutoff Value in DIC Diagnosis>>

Figure 7:
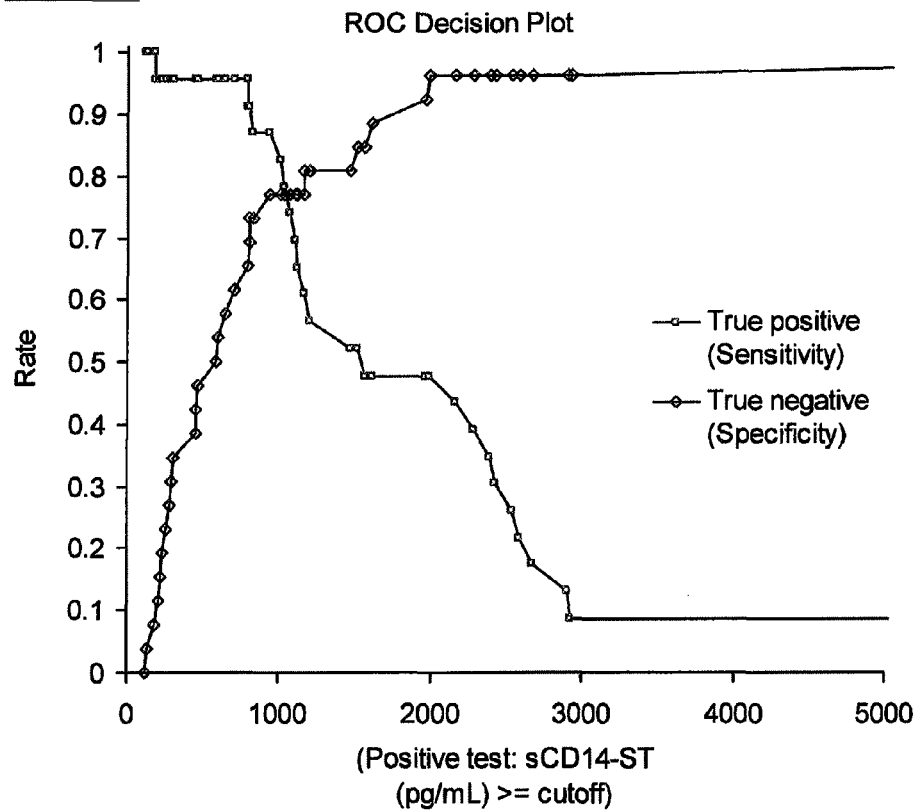
FIG. 7 is a graph showing the clinical sensitivity and specificity of sCD14-ST calculated from the results of ROC analysis on the basis of the diagnostic criteria for JAAM DIC in Example 2. The horizontal axis is the sCD14-ST value, and the vertical axis is sensitivity or specificity.
Figure 8:
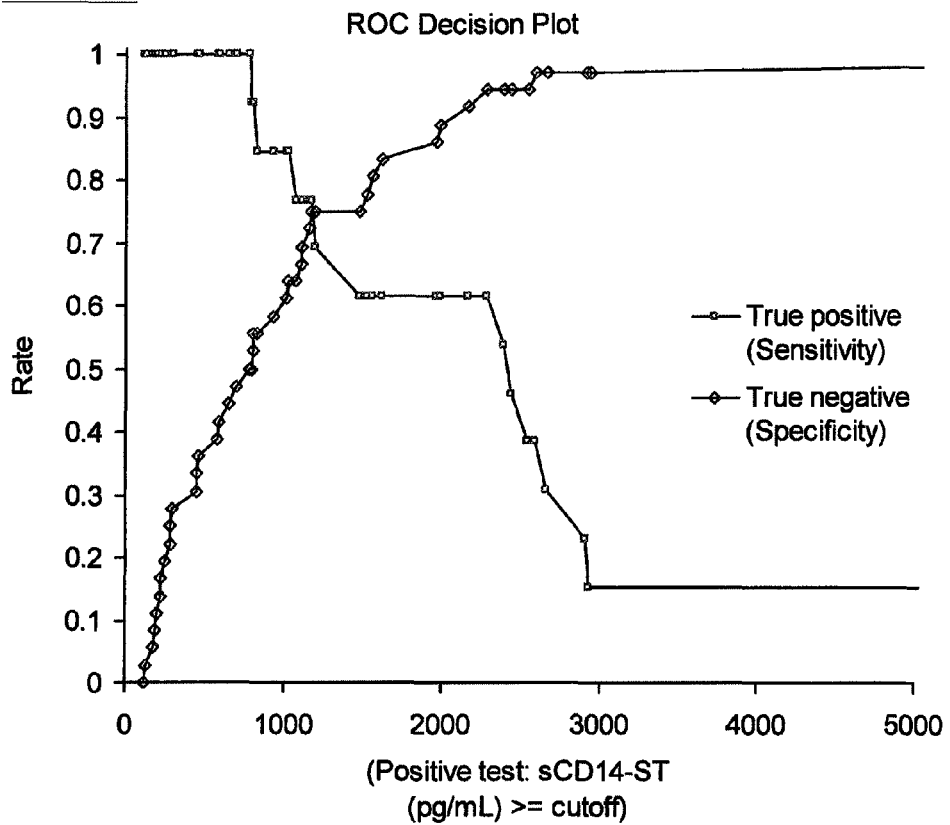
FIG. 8 is a graph showing the clinical sensitivity and specificity of sCD14-ST calculated from the results of ROC analysis on the basis of the Japanese Ministry of Health and Welfare DIC diagnostic criteria in Example 3. The horizontal axis is the sCD14-ST value, and the vertical axis is sensitivity or specificity.

In accordance with the results of the ROC analysis carried out in Examples 2 and 3, the clinical sensitivity and specificity for sCD14-ST are shown in FIGS. 7 and 8, respectively. From FIG. 7, when the sCD14-ST value was 1033 μg/mL, the clinical sensitivity was 78.3% and the specificity was 76.9%, and it was considered to be the optimal cutoff value. From FIG. 8, when the sCD14-ST value was 1170 μg/mL, the clinical sensitivity was 76.9% and the specificity was 75.0%, and it was considered to be the optimal cutoff value. From these results, it is considered that the optimal cutoff value in the method of detecting DIC using sCD14-ST was 1100 μg/mL.

Example 6: Evaluation of D-Dimer Cutoff Value in DIC Diagnosis

Figure 9:
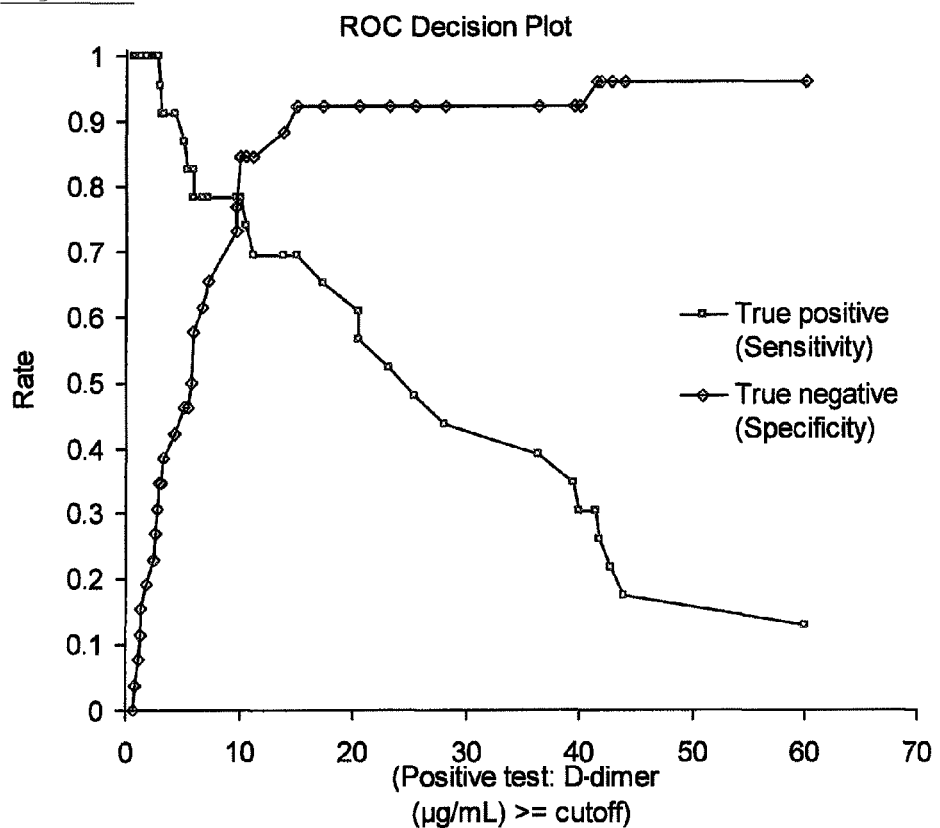
FIG. 9 is a graph showing the clinical sensitivity and specificity of D-dimer calculated from the results of ROC analysis on the basis of the diagnostic criteria for JAAM DIC in Example 2. The horizontal axis is the D-dimer value, and the vertical axis is sensitivity or specificity.
Figure 10:
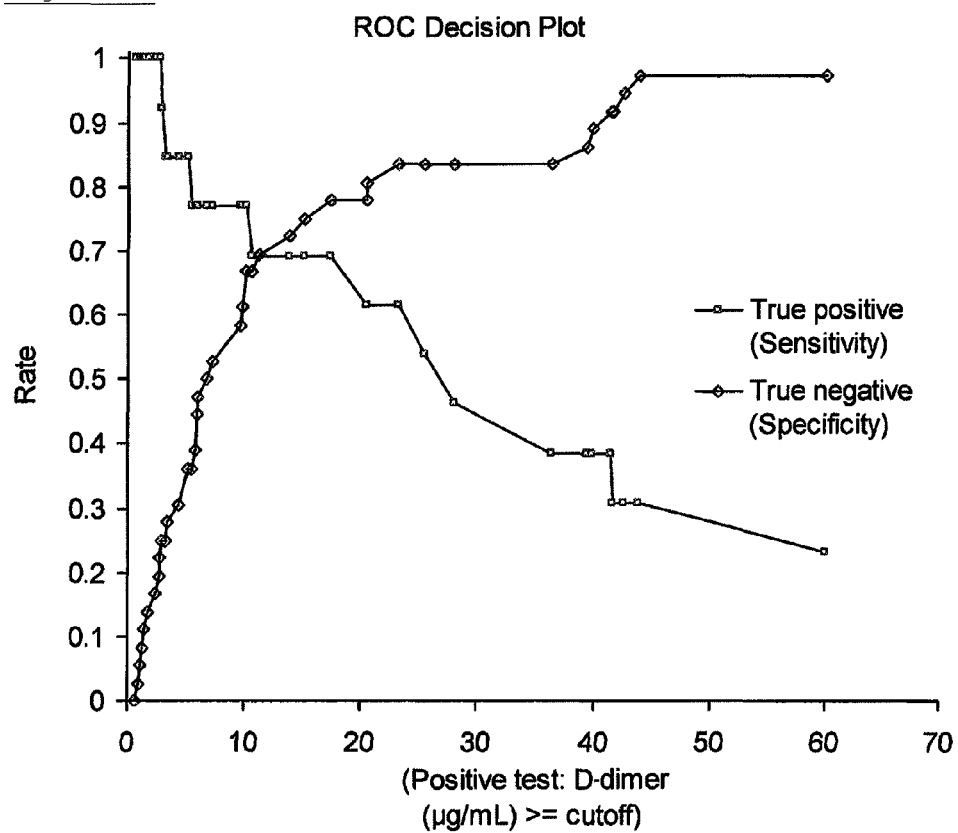
FIG. 10 is a graph showing the clinical sensitivity and specificity of D-dimer calculated from the results of ROC analysis on the basis of the Japanese Ministry of Health and Welfare DIC diagnostic criteria in Example 3. The horizontal axis is the D-dimer value, and the vertical axis is sensitivity or specificity.

In accordance with the results of the ROC analysis carried out in Examples 2 and 3, the clinical sensitivity and specificity for D-dimer are shown in FIGS. 9 and 10, respectively. From FIG. 9, when the D-dimer value was 10.1 μg/mL, the clinical sensitivity was 78.3% and the specificity was 84.6%, and it was considered to be the optimal cutoff value. From FIG. 10, when the D-dimer value was 11.3 μg/mL, the clinical sensitivity was 69.2% and the specificity was 69.4%, and it was considered to be the optimal cutoff value. It was considered from these results that the optimal cutoff value in the method of detecting DIC using D-dimer was 11 μg/mL.

Example 7: Evaluation of FDP Cutoff Value in DIC Diagnosis

Figure 11:
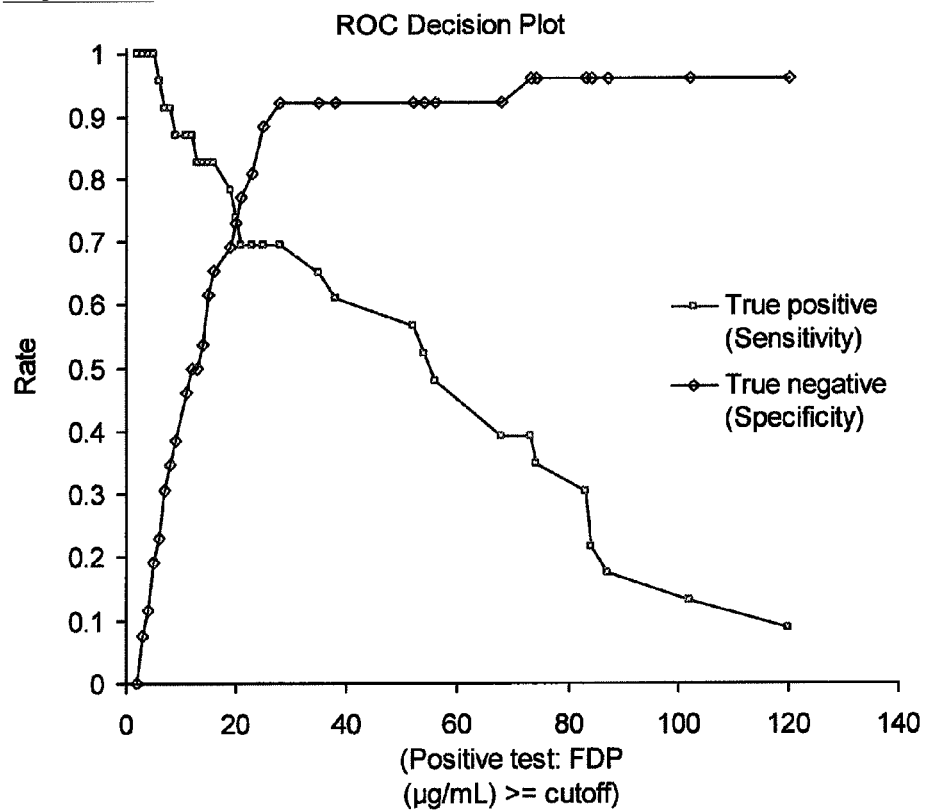
FIG. 11 is a graph showing the clinical sensitivity and specificity of fibrin/fibrinogen degradation products (FDP) calculated from the results of ROC analysis on the basis of the diagnostic criteria for JAAM DIC in Example 2. The horizontal axis is the FDP value, and the vertical axis is sensitivity or specificity.
Figure 12:
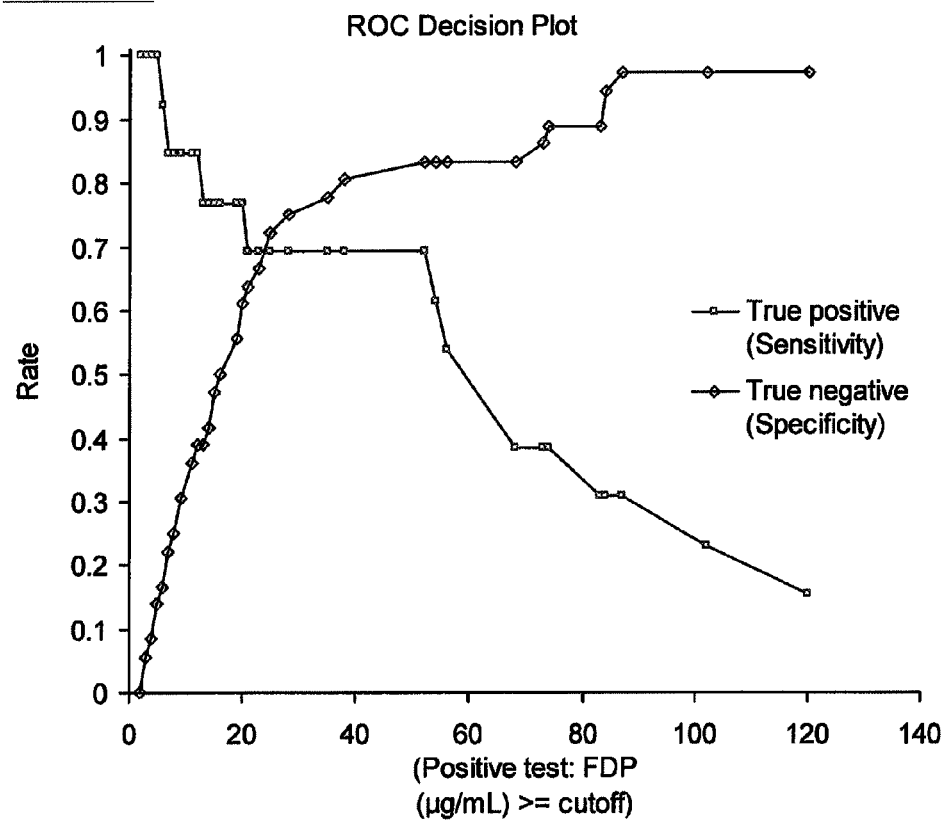
FIG. 12 is a graph showing the clinical sensitivity and specificity of fibrin/fibrinogen degradation products (FDP) calculated from the results of ROC analysis on the basis of the Japanese Ministry of Health and Welfare DIC diagnostic criteria in Example 3. The horizontal axis is the FDP value, and the vertical axis is sensitivity or specificity.

In accordance with the results of the ROC analysis carried out in Examples 2 and 3, the clinical sensitivity and specificity for FDP are shown in FIGS. 11 and 12, respectively. From FIG. 11, when the FDP value was 20 μg/mL, the clinical sensitivity was 73.9% and the specificity was 73.1%, and it was considered to be the optimal cutoff value. From FIG. 12, when the FDP value was 25 μg/mL, the clinical sensitivity was 69.2% and the specificity was 72.2%, and it was considered to be the optimal cutoff value. It was considered from these results that the optimal cutoff value in the method of detecting DIC using FDP was 23 μg/mL.

Example 8: Clinical Sensitivity and Specificity of Each Marker in DIC Diagnosis The cutoff values for sCD14-ST, D-dimer, and fibrin/fibrinogen degradation products (FDP) evaluated in Examples 5 to 7 were used to summarize their clinical sensitivity, specificity, positive predictive value, and negative predictive value, and the result is shown in Table 4. It was confirmed from this result that, even if any one of the diagnostic criteria for JAAM DIC, the Japanese Ministry of Health and Welfare DIC diagnostic criteria, and the ISTH overt-DIC diagnostic criteria is used, sCD14-ST was equivalent or superior to conventional markers, such as D-dimer or FDP, and was useful because, in particular, the sensitivity and negative predictive value were high.

TABLE 4

| DIC diagnostic criteria | Marker | Cutoff value | Sensitivity | Specificity | Positive predictive value | Negative predictive value |
|---|---|---|---|---|---|---|
| Diagnostic criteria for JAAM DIC | sCD14-ST | 1100 pg/mL | 82.6% | 76.9% | 76.0% | 83.3% |
| | D-dimer | 11 μg/mL | 69.6% | 84.6% | 80.0% | 75.9% |
| | FDP | 23 μg/mL | 69.6% | 80.8% | 76.2% | 75.0% |
| JMHW DIC diagnostic criteria | sCD14-ST | 1100 pg/mL | 76.9% | 66.7% | 45.5% | 88.9% |
| | D-dimer | 11 μg/mL | 69.2% | 69.4% | 45.0% | 86.2% |
| | FDP | 23 μg/mL | 69.2% | 66.7% | 42.9% | 85.7% |
| ISTH overt-DIC diagnostic criteria | sCD14-ST | 1100 pg/mL | 80.0% | 70.6% | 54.5% | 88.9% |
| | D-dimer | 11 μg/mL | 73.3% | 73.5% | 55.0% | 86.2% |
| | FDP | 23 μg/mL | 73.3% | 70.6% | 52.4% | 85.7% |

JMHW: Japanese Ministry of Health and Welfare

Example 9: Usefulness for DIC Diagnosis in Uninfected Group

Figure 13:
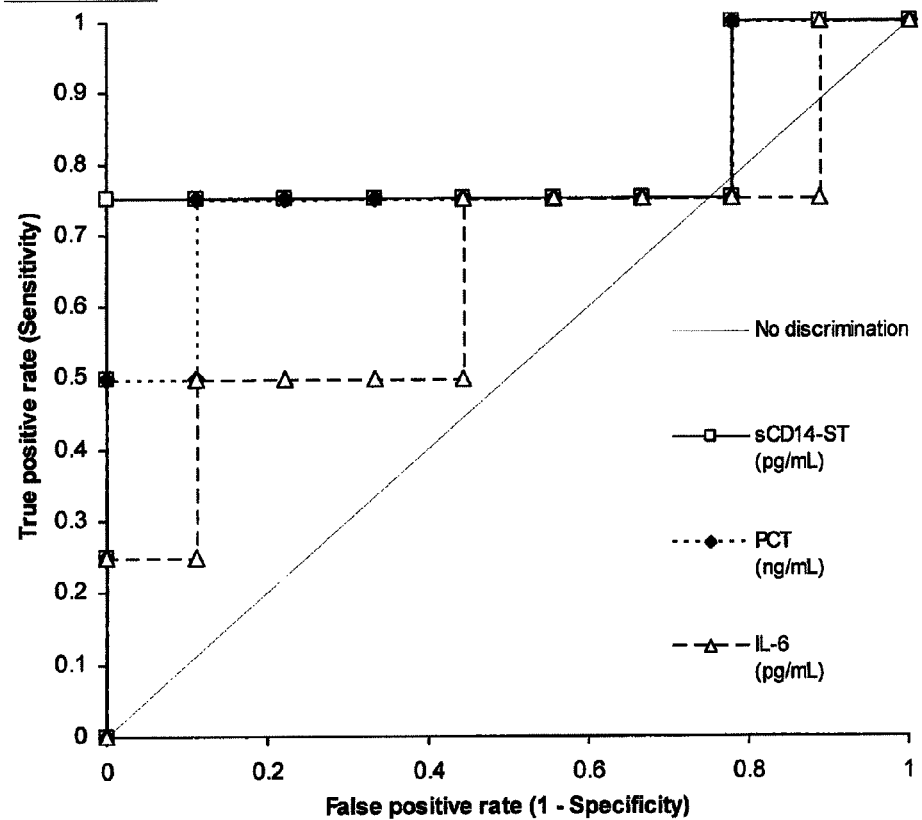
FIG. 13 is a graph showing the results of ROC analysis. Among patients (49 cases) registered in a clinical study, 13 uninfected cases (SIRS and noninfectious diseases) were classified into a DIC group (4 cases) and a non-DIC group (9 cases) on the basis of the diagnostic criteria for JAAM DIC, and each usefulness for DIC detection of sCD14-ST, procalcitonin (PCT), and interleukin-6 (IL-6) in samples collected on admission was compared to one another by ROC analysis.
Figure 14:
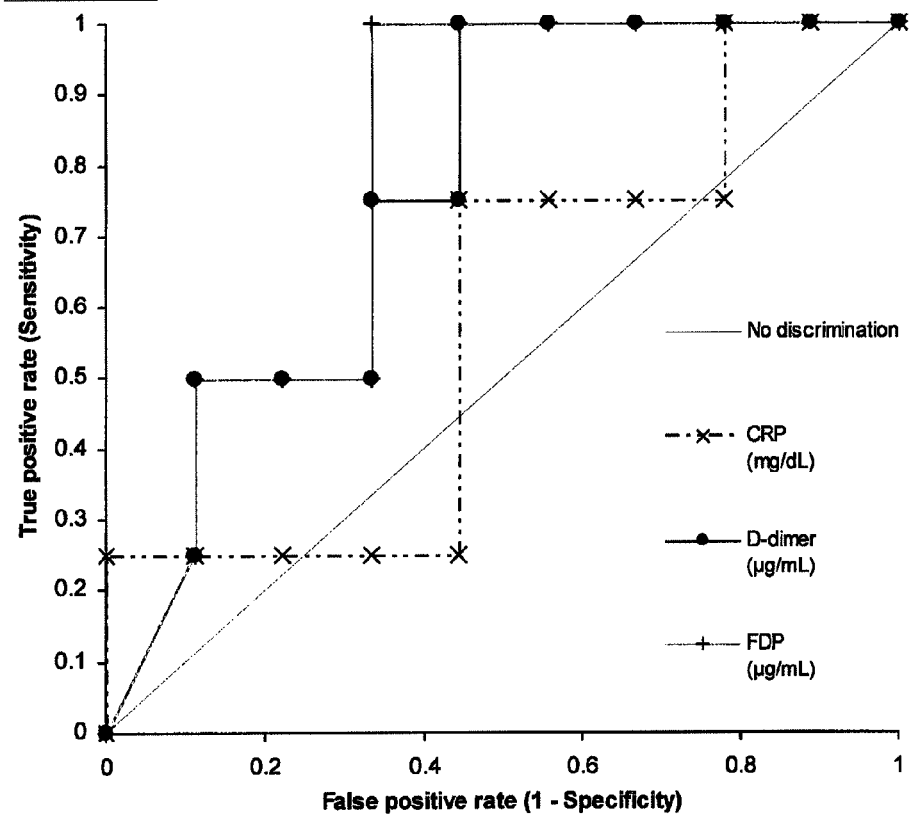
FIG. 14 is a graph showing the results of ROC analysis. With respect to the patients classified in a similar fashion to those in FIG. 13, each usefulness for DIC detection of C-reactive protein (CRP), D-dimer, and fibrin/fibrinogen degradation products (FDP) in samples collected on admission was compared to one another by ROC analysis.
Figure 15:
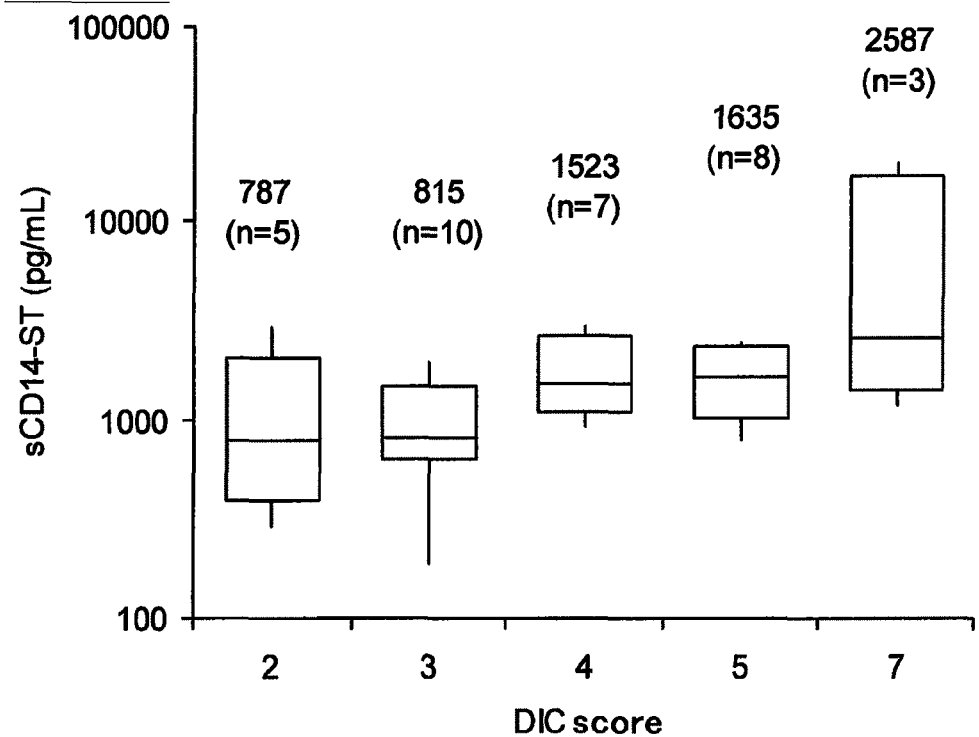
FIG. 15 is a box-and-whisker plot showing the results of the comparison of the measured value distribution of sCD14-ST for each DIC score. Among patients (49 cases) registered in a clinical study, with respect to 33 infected cases (sepsis, severe sepsis, septic shock, and infectious diseases), a DIC score was calculated, and sCD14-ST was measured, and the distribution of the measured sCD14-ST values for each DIC score was compared to one another.
Figure 16:
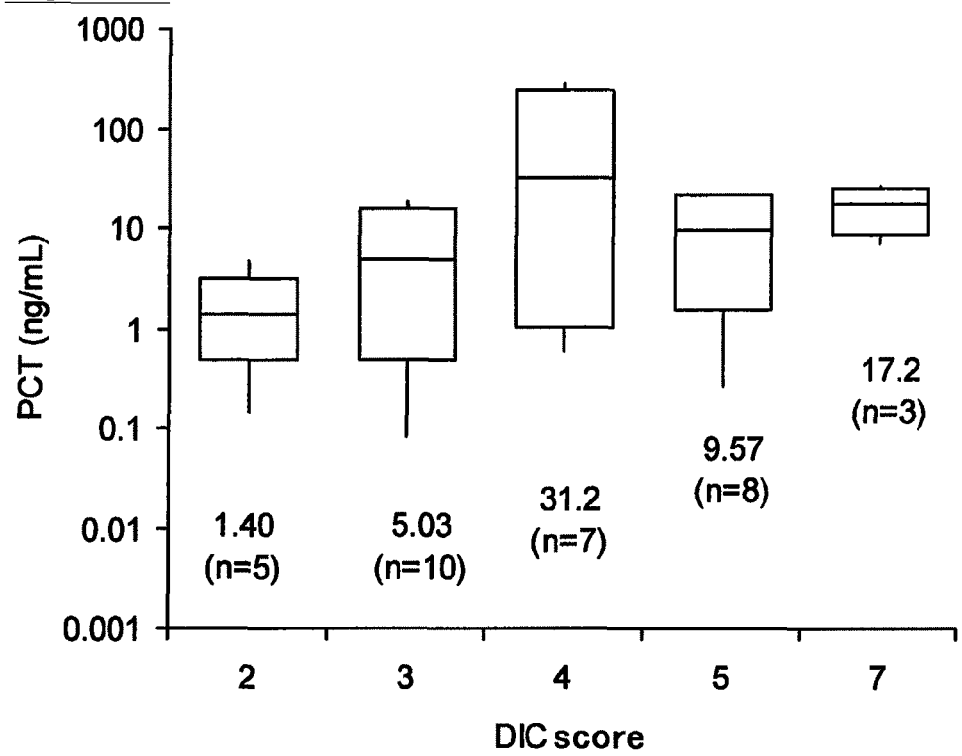
FIG. 16 is a box-and-whisker plot showing the results of the comparison of the measured value distribution of procalcitonin (PCT) for each DIC score. With respect to the same 33 cases as those of FIG. 15, a DIC score was calculated, and PCT was measured, and the distribution of the measured PCT values for each DIC score was compared to one another.
Figure 17:
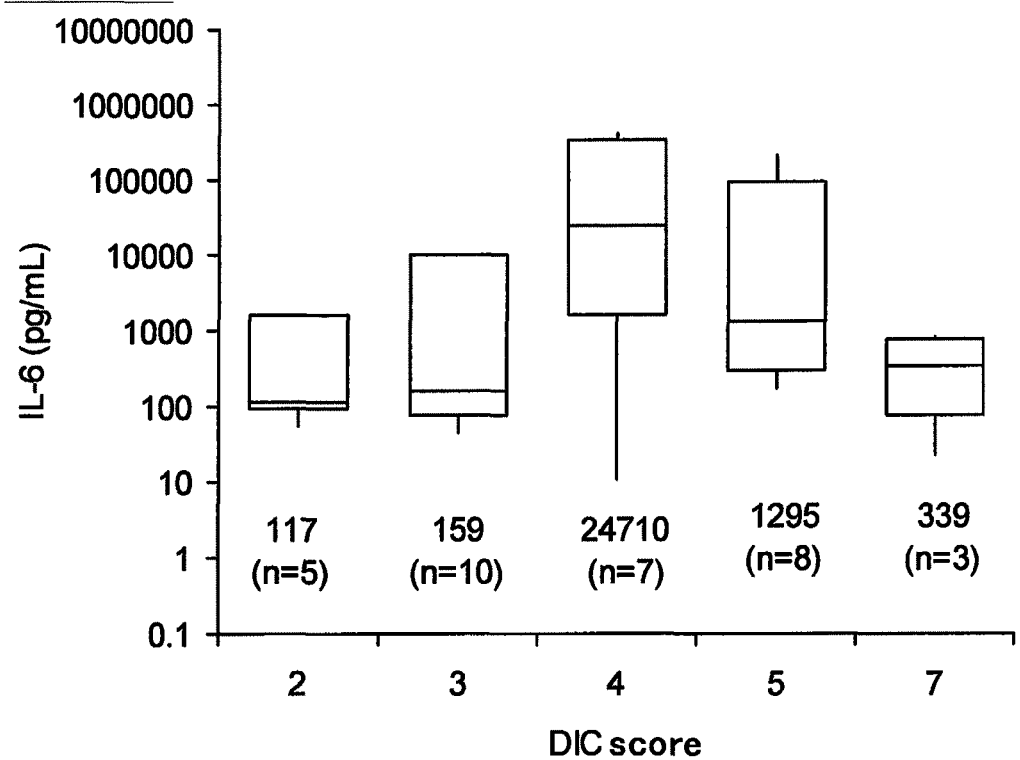
FIG. 17 is a box-and-whisker plot showing the results of the comparison of the measured value distribution of C-reactive protein (CRP) for each DIC score. With respect to the same 33 cases as those of FIG. 15, a DIC score was calculated, and CRP was measured, and the distribution of the measured CRP values for each DIC score was compared to one another.
Figure 18:
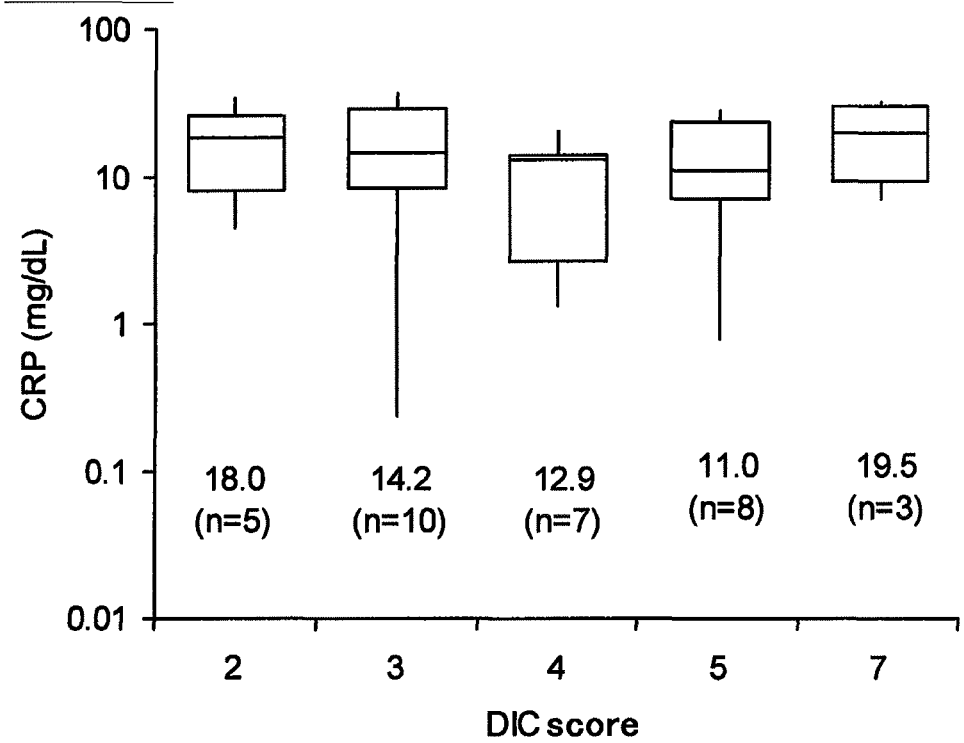
FIG. 18 is a box-and-whisker plot showing the results of the comparison of the measured value distribution of interleukin-6 (IL-6) for each DIC score. With respect to the same 33 cases as those of FIG. 15, a DIC score was calculated, and IL-6 was measured, and the distribution of the measured IL-6 values for each DIC score was compared to one another.

Among the 49 cases in Example 2, 13 uninfected cases (SIRS and noninfectious diseases) were classified into a DIC group (4 cases) and a non-DIC group (9 cases), on the basis of the diagnostic criteria for JAAM DIC, and each usefulness of sCD14-ST, procalcitonin (PCT), C-reactive protein (CRP), interleukin-6 (IL-6), D-dimer, and fibrin/fibrinogen degradation products (FDP) for DIC detection was compared to one another by ROC analysis. The results are shown in FIGS. 13 and 14. In FIGS. 13 and 14, the horizontal axis is the "1-specificity", and the vertical axis is "sensitivity".

The calculated AUCs were 0.806 (sCD14-ST), 0.778 (PCT), 0.639 (IL-6), 0.583 (CRP), 0.764 (D-dimer), and 0.792 (FDP), and the AUC of sCD14-ST was the highest. It was confirmed from this result that sCD14-ST is more useful than conventional markers, such as D-dimer, FDP, and the like, regardless of the presence or absence of infection. With respect to an sCD14-ST cutoff value, when the sCD14-ST value was 600 μg/mL, the clinical sensitivity was 75.0% and the specificity was 100%, and it was considered to be the optimal cutoff value.

Example 10: Usefulness of Each Marker as Index for Carrying Out Anticoagulant Therapy for DIC Patients Among the 49 cases in Example 2, a DIC group (23 cases) classified on the basis of the diagnostic criteria for JAAM DIC was used to compare implementation rates of anticoagulant therapy to one another in cases in which each marker was lower than its cutoff value or was equal to or higher than its cutoff value, and the results are shown in Table 5. From these results, with respect to sCD14-ST, the implementation rate of anticoagulant therapy was higher in the case group in which the sCD14-ST value was equal to or higher than its cutoff value, in comparison with another case group in which the sCD14-ST value was lower than its cutoff value. By contrast, with respect to D-dimer or FDP, the implementation rate of anticoagulant therapy was lower in the case group in which each value was equal to or higher than its cutoff value, in comparison with another case group in which each value was lower than its cutoff value. Therefore, it was suggested that sCD14-ST was a useful marker than conventional DIC markers, such as D-dimer and FDP, as an index as to whether or not anticoagulant therapy should be carried out.

TABLE 5

| Marker | | sCD14-ST | D-dimer | FDP |
|---|---|---|---|---|
| Cutoff value | | 1100 pg/mL | 11 μg/mL | 23 μg/mL |
| Cases where anticoagulant therapy was carried out | Lower than cutoff value | 28.6% (2/7) | 57.1% (4/7) | 57.1% (4/7) |
| | Equal to or higher than cutoff value | 50.0% (8/16) | 37.5% (6/16) | 37.5% (6/16) |

Example 11: Measured Value Distribution of Sepsis Markers for Each DIC Score in Infected Group Among the 49 cases registered in this study, with respect to 33 infected cases (sepsis, severe sepsis, septic shock, and infectious diseases), the DIC score was calculated on the basis of the diagnostic criteria for JAAM DIC, and each measured value distribution of sCD14-ST, procalcitonin (PCT), C-reactive protein (CRP), and interleukin-6 (IL-6) in each DIC score was compared to one another. The measurement of sCD14-ST was carried out in accordance with Example 1.

As a result of a multiple-group statistical analysis by the Kruskal-Wallis test, as shown in Table 6, the p value of sCD14-ST was 0.0214, the p value of PCT was 0.0436, the p value of IL-6 was 0.0729, and the p value of CRP was 0.3994, and thus, there were significant differences between sCD14-ST and each of PCT, IL-6, and CRP. It was considered that sCD14-ST was a marker that most closely reflected the infectious DIC score. FIGS. 15 to 18 show the medians and the numbers of cases of each marker in each DIC score.

TABLE 6

| | Sepsis marker | Significant difference (p value) |
|---|---|---|
| (A) | sCD14-ST | 0.0214 |
| (B) | PCT | 0.0436 |
| (C) | IL-6 | 0.0729 |
| (D) | CRP | 0.3994 |

With respect to sCD14-ST and PCT in which significant difference was confirmed by the multiple-group statistical analysis, the same patient group was classified into an infectious non-DIC group (DIC score: less than 4 points; n=15) and an infectious DIC group (DIC score: 4 points or higher; n=18), and the measured values of sCD14-ST and PCT in each group were used to carry out two-group statistical analysis by the Mann-Whitney U test. As a result, the p value of sCD14-ST was 0.0075, and the p value of PCT was 0.0329, and thus, it was shown that sCD14-ST was most useful in detecting the infectious DIC.

Since the sCD14-ST value was elevated in accordance with the increase of the DIC score, it was suggested that the degree of DIC can be recognized from the sCD14-ST value.

Example 12: Evaluation of sCD14-ST for the Detection Performance of Infection and Cutoff Value>>

Figure 19:
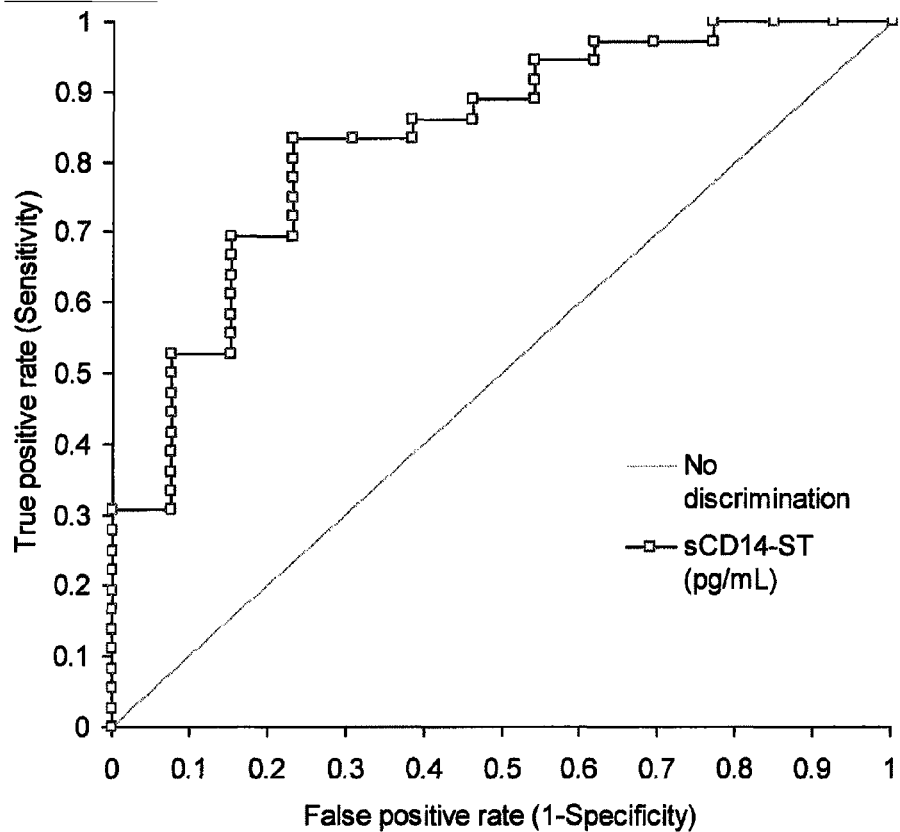
FIG. 19 is a graph showing the results of ROC analysis. Patients (49 cases) registered in a clinical study were classified into 13 uninfected cases (SIRS and noninfectious diseases) and 36 infected cases (sepsis, severe sepsis, septic shock, and infectious diseases), and the usefulness of sCD14-ST for infection detection was evaluated by ROC analysis.

The 49 cases registered in this study were classified into 13 uninfected cases (SIRS and noninfectious diseases) and 36 infected cases (sepsis, severe sepsis, septic shock, and infectious diseases), and the usefulness of sCD14-ST for infection detection was evaluated by ROC analysis. In FIG. 19, the horizontal axis is the "1-specificity", and the vertical axis is "sensitivity".

The AUC of sCD14-ST was 0.833, and its usefulness was confirmed. The sCD14-ST value in which the clinical sensitivity and specificity became maximum was 647 μg/mL, and the clinical sensitivity and the specificity were 83.3% and 76.9%, respectively. It was considered from these results that the optimal cutoff value of sCD14-ST in infection detection was 600 to 700 μg/mL.

Example 13: Evaluation of sCD14-ST for the Detection Performance of DIC and Cutoff Value in Infected Group>>

Figure 20:
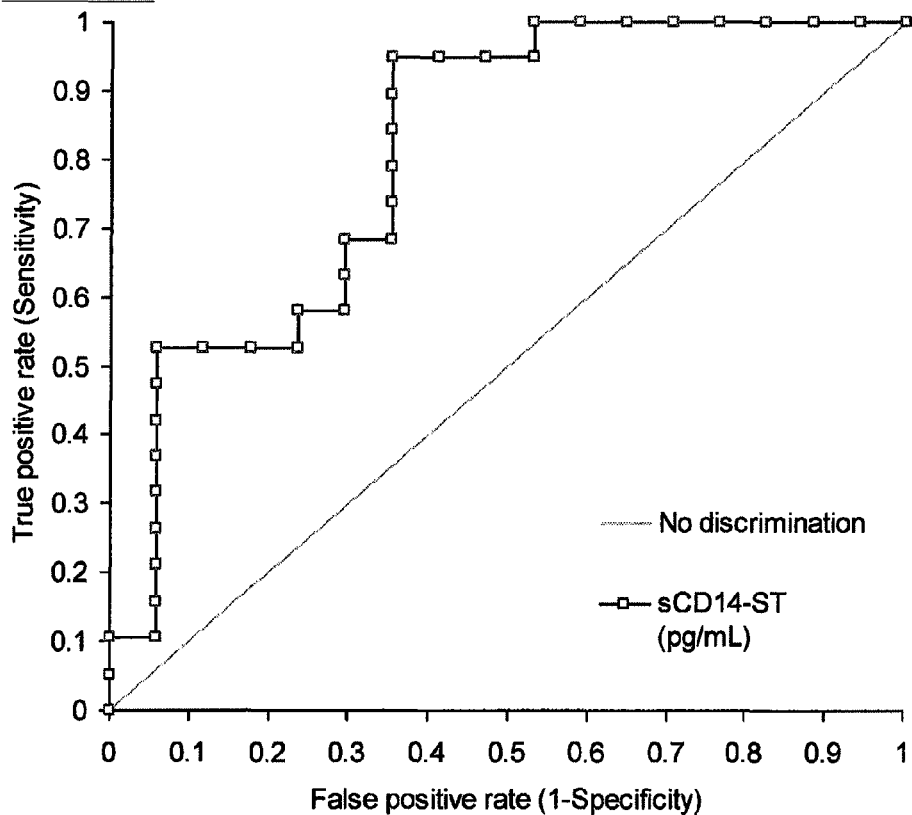
FIG. 20 is a graph showing the results of ROC analysis. Among patients (49 cases) registered in a clinical study, 36 infected cases (sepsis, severe sepsis, septic shock, and infectious diseases) were classified into a DIC group (19 cases) and a non-DIC group (17 cases) on the basis of the diagnostic criteria for JAAM DIC, and the usefulness of sCD14-ST for infectious DIC detection was evaluated by ROC analysis.
Figure 21:
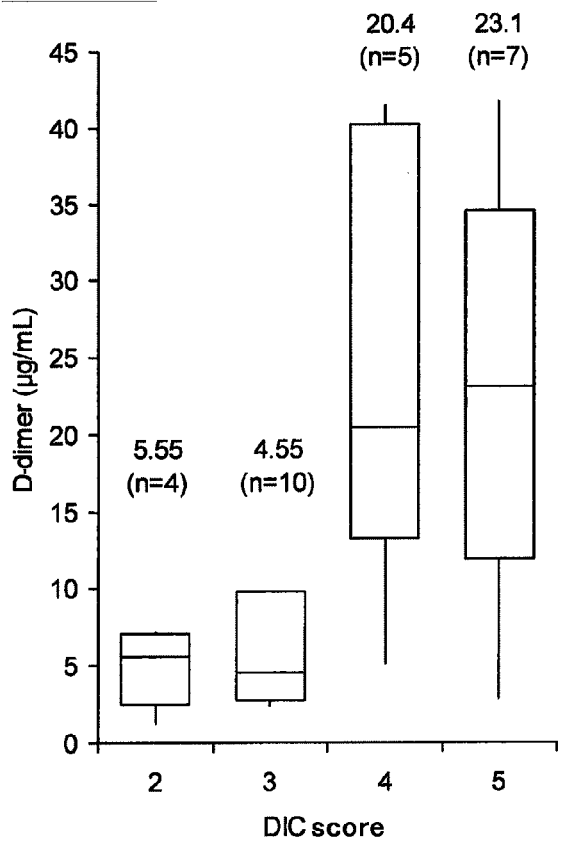
FIG. 21 is a box-and-whisker plot showing the results of the comparison of the measured value distribution of D-dimer for each DIC score. Among patients (49 cases) registered in the clinical study, with respect to 26 infected cases (sepsis, severe sepsis, septic shock, and infectious diseases), a DIC score was calculated, and a D-dimer was measured, and the distribution of the measured D-dimer values for each DIC score was compared to one another.
Figure 22:
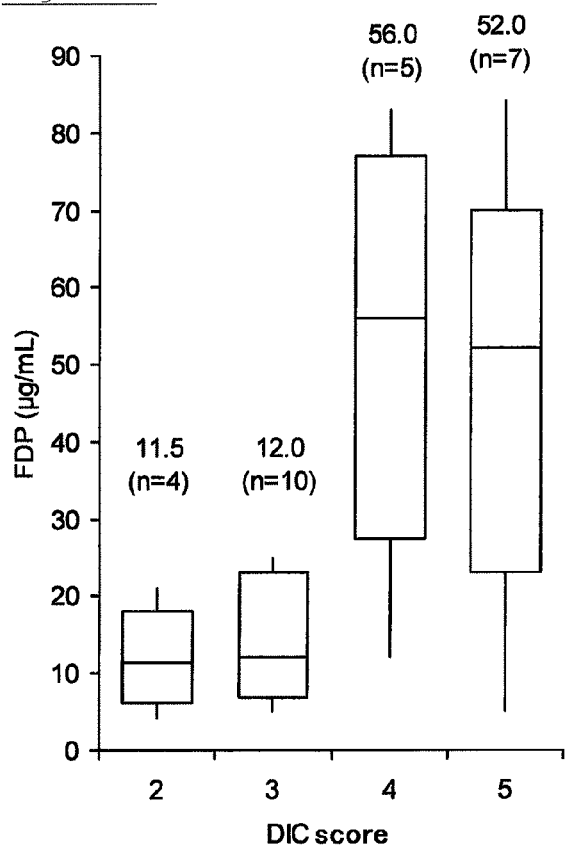
FIG. 22 is a box-and-whisker plot showing the results of the comparison of the measured value distribution of fibrin/fibrinogen degradation products (FDP) for each DIC score. With respect to the same 26 cases as those of FIG. 21, a DIC score was calculated, and FDP was measured, and the distribution of the measured FDP values for each DIC score was compared to one another.
Figure 23:
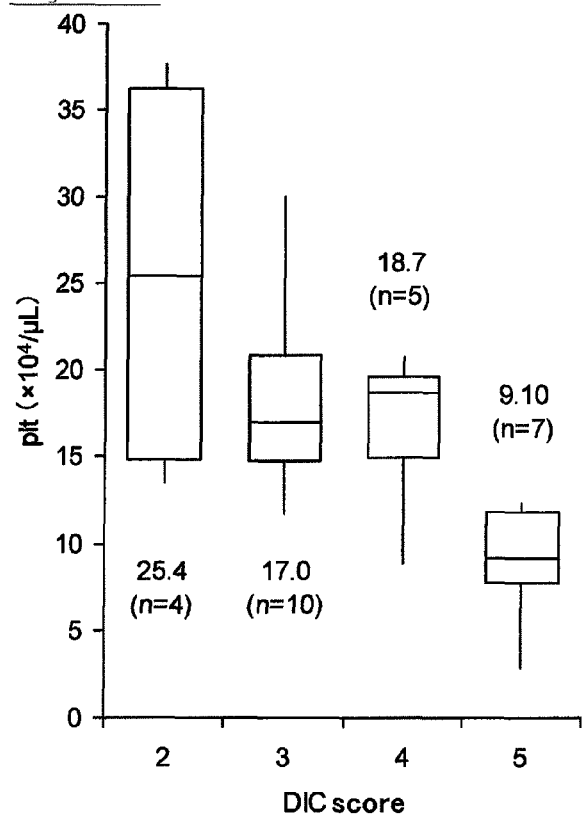
FIG. 23 is a box-and-whisker plot showing the results of the comparison of the measured value distribution of platelets (Pit) for each DIC score. With respect to the same 26 cases as those of FIG. 21, a DIC score was calculated, and a platelet was measured, and the distribution of the measured platelet values for each DIC score was compared to one another.
Figure 24:
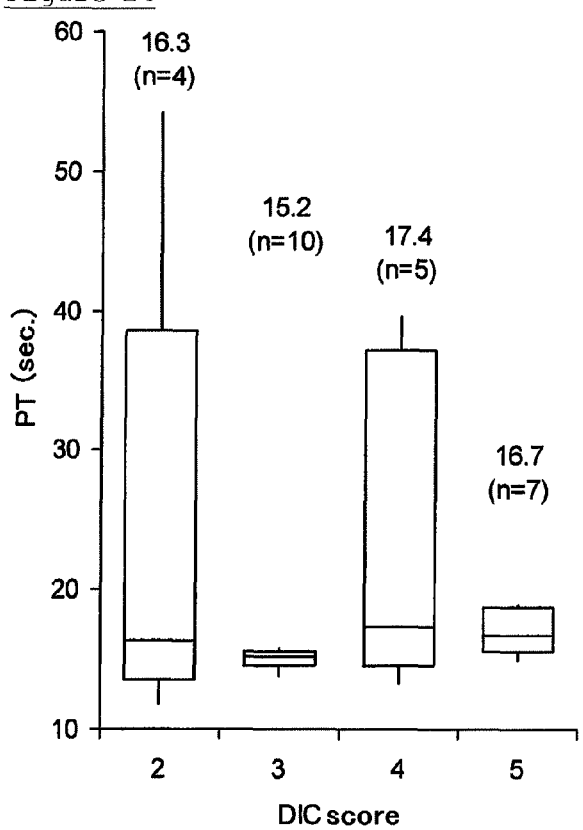
FIG. 24 is a box-and-whisker plot showing the results of the comparison of the measured value distribution of prothrombin time (PT)(sec.) for each DIC score. With respect to the same 26 cases as those of FIG. 21, a DIC score was calculated, and PT (sec.) was measured, and the distribution of the measured PT (sec.) values for each DIC score was compared to one another.
Figure 25:
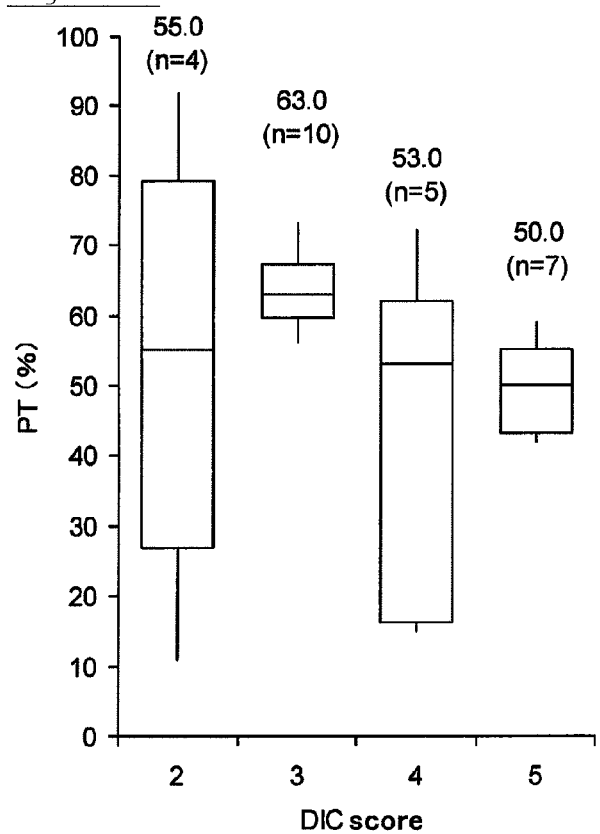
FIG. 25 is a box-and-whisker plot showing the results of the comparison of the measured value distribution of prothrombin time (PT)(%) for each DIC score. With respect to the same 26 cases as those of FIG. 21, a DIC score was calculated, and PT (%) was measured, and the distribution of the measured PT (%) values for each DIC score was compared to one another.
Figure 26:
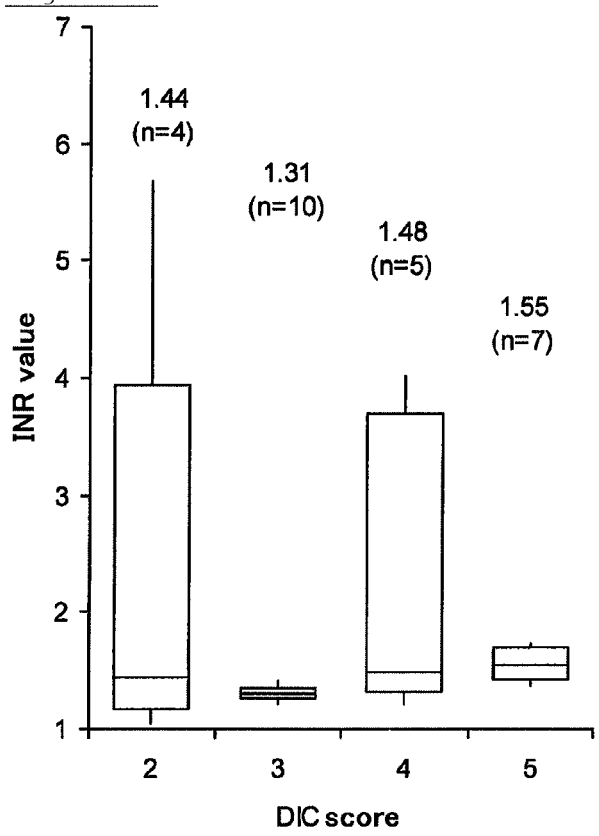
FIG. 26 is a box-and-whisker plot showing the results of the comparison of the measured value distribution of INR for each DIC score. With respect to the same 26 cases as those of FIG. 21, a DIC score was calculated, and INR was measured, and the distribution of the measured INR values for each DIC score was compared to one another.
Figure 27:
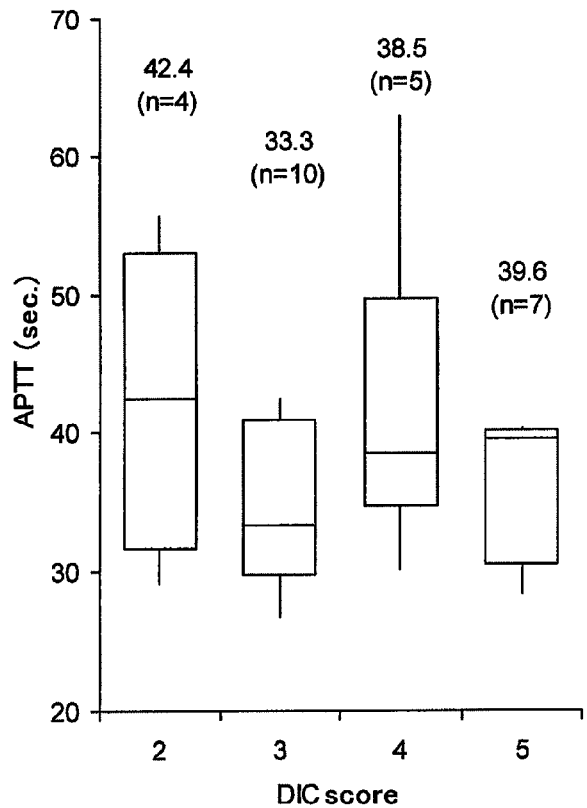
FIG. 27 is a box-and-whisker plot showing the results of the comparison of the measured value distribution of activated partial thromboplastin time (APTT) for each DIC score. With respect to the same 26 cases as those of FIG. 21, a DIC score was calculated, and APTT was measured, and the distribution of the measured APTT values for each DIC score was compared to one another.
Figure 28:
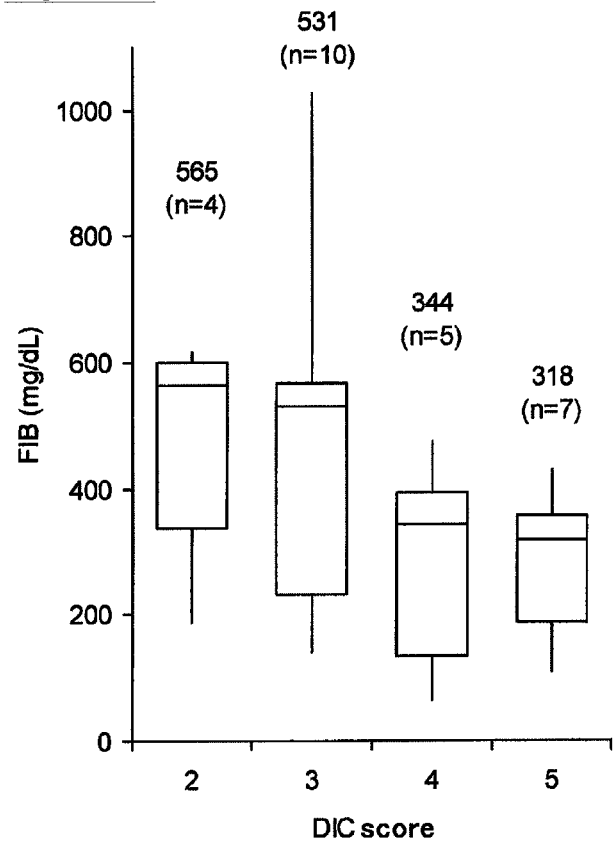
FIG. 28 is a box-and-whisker plot showing the results of the comparison of the measured value distribution of fibrinogen (FIB) for each DIC score. With respect to the same 26 cases as those of FIG. 21, a DIC score was calculated, and FIB was measured, and the distribution of the measured FIB values for each DIC score was compared to one another.
Figure 29:
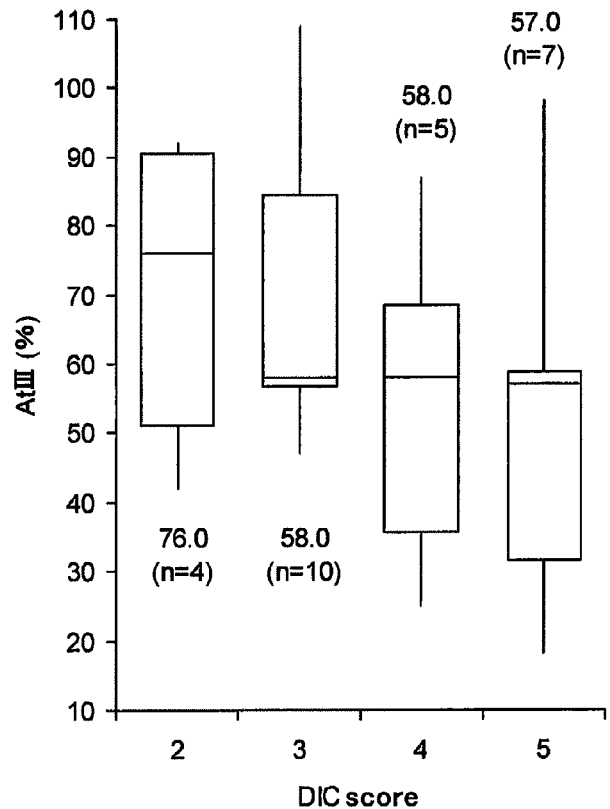
FIG. 29 is a box-and-whisker plot showing the results of the comparison of the measured value distribution of antithrombin III (ATIII) for each DIC score. With respect to the same 26 cases as those of FIG. 21, a DIC score was calculated, and ATIII was measured, and the distribution of the measured ATIII values for each DIC score was compared to one another.
Figure 30:
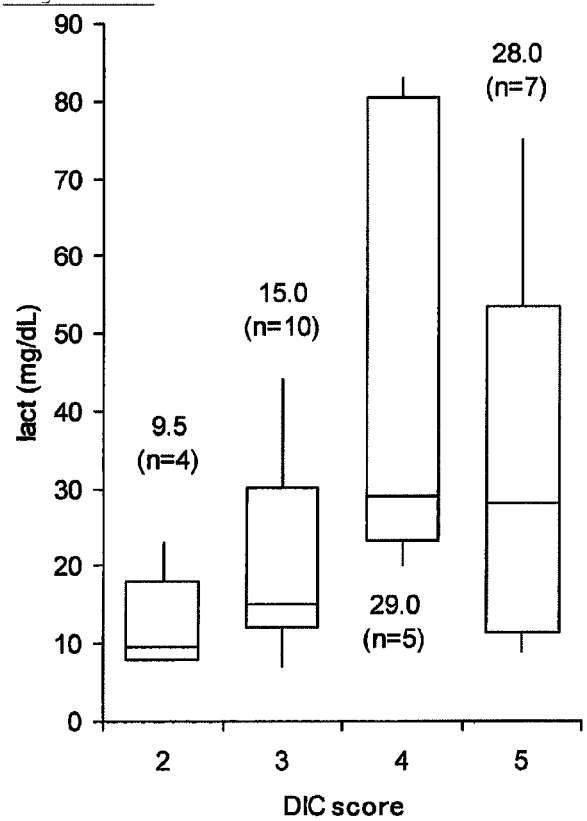
FIG. 30 is a box-and-whisker plot showing the results of the comparison of the measured value distribution of lactate (Lact) for each DIC score. With respect to the same 26 cases as those of FIG. 21, a DIC score was calculated, and Lact was measured, and the distribution of the measured Lact values for each DIC score was compared to one another.
Figure 31:
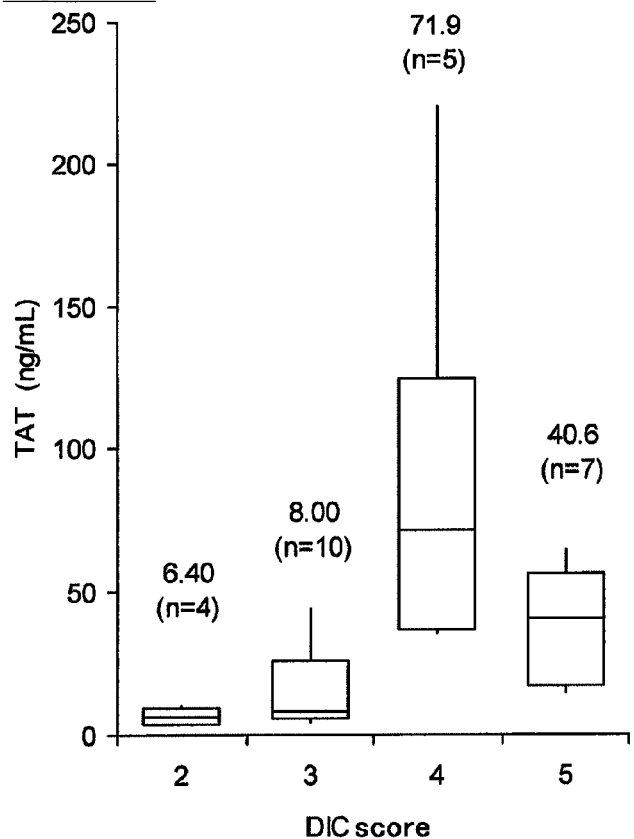
FIG. 31 is a box-and-whisker plot showing the results of the comparison of the measured value distribution of thrombin-antithrombin III complex (TAT) for each DIC score. With respect to the same 26 cases as those of FIG. 21, a DIC score was calculated, and TAT was measured, and the distribution of the measured TAT values for each DIC score was compared to one another.
Figure 32:
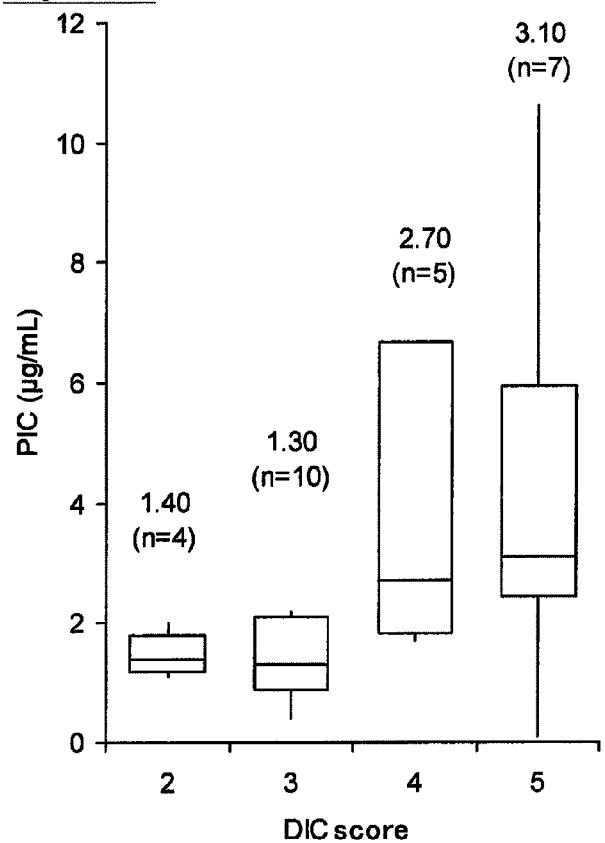
FIG. 32 is a box-and-whisker plot showing the results of the comparison of the measured value distribution of α2-plasmin inhibitor/plasmin complex (PIC) for each DIC score. With respect to the same 26 cases as those of FIG. 21, a DIC score was calculated, and PIC was measured, and the distribution of the measured PIC values for each DIC score was compared to one another.
Figure 33:
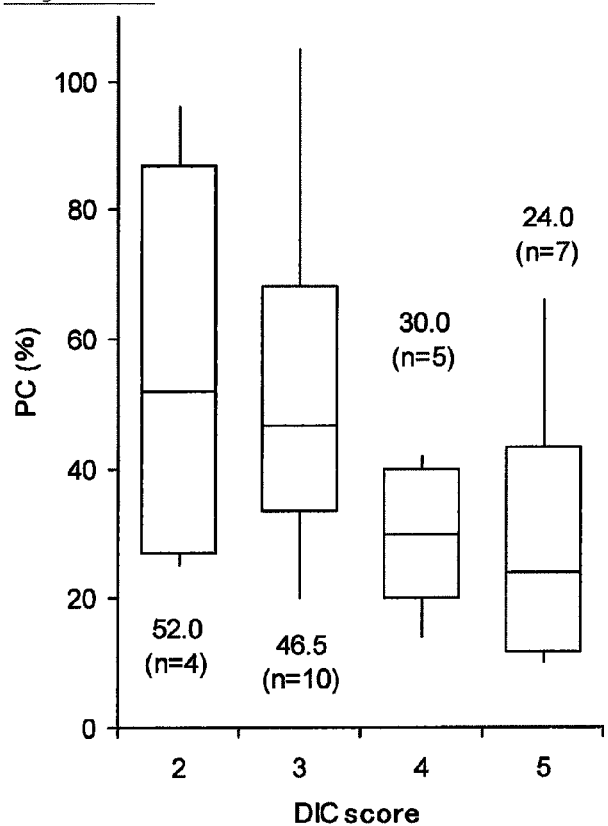
FIG. 33 is a box-and-whisker plot showing the results of the comparison of the measured value distribution of protein C (PC) for each DIC score. With respect to the same 26 cases as those of FIG. 21, a DIC score was calculated, and PC was measured, and the distribution of the measured PC values for each DIC score was compared to one another.
Figure 34:
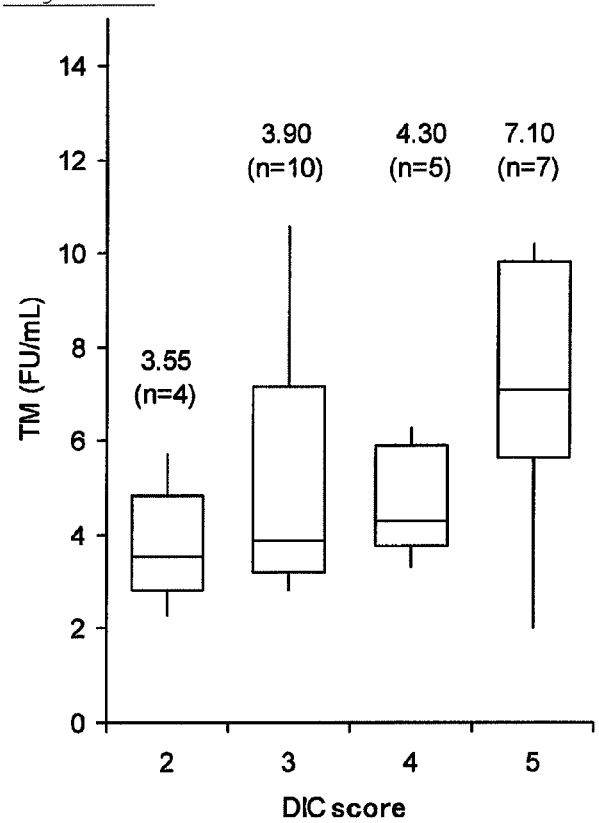
FIG. 34 is a box-and-whisker plot showing the results of the comparison of the measured value distribution of thrombomodulin (TM) for each DIC score. With respect to the same 26 cases as those of FIG. 21, a DIC score was calculated, and TM was measured, and the distribution of the measured TM values for each DIC score was compared to one another.
Figure 35:
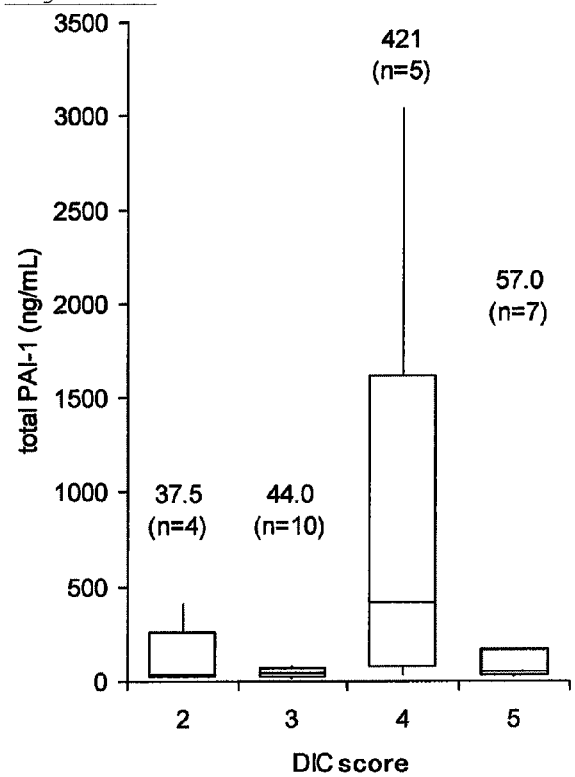
FIG. 35 is a box-and-whisker plot showing the results of the comparison of the measured value distribution of tissue plasminogen activator (tPA)/plasminogen activator inhibitor (PAI-1) complex (Total PAI-1) for each DIC score. With respect to the same 26 cases as those of FIG. 21, a DIC score was calculated, and Total PAI-1 was measured, and the distribution of the measured Total PAI-1 values for each DIC score was compared to one another.

Among the 49 cases registered in this study, 36 infected cases (sepsis, severe sepsis, septic shock, and infectious diseases) were classified into a DIC group (19 cases) and a non-DIC group (17 cases), on the basis of the diagnostic criteria for JAAM DIC, and the usefulness of sCD14-ST for infectious DIC detection was evaluated by ROC analysis. In FIG. 20, the horizontal axis is the "1-specificity", and the vertical axis is "sensitivity".

The AUC of sCD14-ST was 0.811, and its usefulness was confirmed. The sCD14-ST value in which the clinical sensitivity and specificity became maximum was 929 μg/mL, and the clinical sensitivity and the specificity were 94.7% and 64.7%, respectively. It was considered from these results that the optimal cutoff value of sCD14-ST in infectious DIC detection was 900 to 1000 μg/mL.

Example 14: Measured Value Distribution of Coagulation-Related Markers for Each DIC Score in Infected Group Among the 49 cases registered in this study, with respect to 26 infected cases (sepsis, severe sepsis, septic shock, and infectious diseases), each measured value distribution of D-dimer, fibrin/fibrinogen degradation products (FDP), platelet (Plt), prothrombin time (PT), INR value, activated partial thromboplastin time (APTT), fibrinogen (FIB), antithrombin III (ATIII), lactate (Lact), thrombin-antithrombin complex (TAT), α2-plasmin inhibitor/plasmin complex (PIC), protein C (PC), thrombomodulin (TM), and tissue plasminogen activator (tPA)/plasminogen activator inhibitor (PAI-1) complex (Total PAI-1) in each DIC score was compared to one another.

D-dimer was measured using Nanopia D-dimer (Sekisui Medical Co., Ltd.). FDP was measured using Nanopia p-FDP (Sekisui Medical Co., Ltd.). Platelet was measured using Cell pack II (Sysmex Corporation). PT was measured using Coagpia PT-S(Sekisui Medical Co., Ltd.). APTT was measured using Coagpia APTT-S(Sekisui Medical Co., Ltd.). Fibrinogen was measured using Coagpia Fbg (Sekisui Medical Co., Ltd.). Antithrombin III was measured using STACIA CLEIA TAT (LSI Medience Corporation). Lactate was measured using Determiner LA (Kyowa Medex Co., Ltd.). TAT was measured using STACIA CLEIA TAT (LSI Medience Corporation). PIC was measured using LPIA-ACE PPI II (LSI Medience Corporation). Protein C was measured using LPIA-ACE PC II (LSI Medience Corporation). Thrombomodulin was measured using STACIA CLEIA TM (LSI Medience Corporation). Total PAI-1 was measured using LPIA tPAI test (LSI Medience Corporation).

The results of the multiple-group statistical analysis by the Kruskal-Wallis test are shown in Table 7. It was considered that D-dimer, FDP, platelet, and TAT were markers that reflected the infectious DIC score. FIGS. 21 to 35 show the medians and the numbers of cases of each marker in each DIC score.

TABLE 7

|  | Coagulation-related marker | Significant difference (p value) |
|---|---|---|
| (A) | D-dimer | 0.0247 |
| (B) | FDP | 0.0365 |
| (C) | Platelet | 0.0443 |
| (D) | PT (sec.) | 0.3213 |
| (E) | PT (%) | 0.1325 |
| (F) | INR value | 0.1150 |
| (G) | APTT | 0.6533 |
| (H) | Fibrinogen | 0.1239 |
| (I) | Antithrombin III | 0.3493 |
| (J) | Lactate | 0.0629 |
| (K) | TAT | 0.0027 |
| (L) | PIC | 0.0585 |
| (M) | Protein C | 0.0904 |
| (N) | Thrombomodulin | 0.2304 |
| (O) | Total PAI-1 | 0.1141 |

With respect to D-dimer, FDP, platelet, and TAT in which significant difference was confirmed by the multiple-group statistical analysis, the same patient group was classified into an infectious non-DIC group (DIC score: less than 4 points; n=14) and an infectious DIC group (DIC score: 4 points or higher; n=12), and the measured values of D-dimer, FDP, platelet, and TAT in each group were used to carry out two-group statistical analysis by the Mann-Whitney U test. As a result, the p value of D-dimer was 0.0017, the p value of FDP was 0.0037, the p value of platelet was 0.0464, and the p value of TAT was 0.0002, and thus, it was shown that D-dimer, FDP, platelet, and TAT were useful in detecting the infectious DIC.

Example 15: Evaluation of the Combination of sCD14-ST with Coagulation-Related Markers for the Detection Performance of Infectious DIC>>

Among the 49 cases registered in this study, with respect to 44 cases in which all the measured values for sepsis markers [sCD14-ST, procalcitonin (PCT), interleukin-6 (IL-6), and C-reactive protein (CRP)] and coagulation-related markers [D-dimer, fibrin/fibrinogen degradation products (FDP), platelet (Plt), prothrombin time (PT), INR value, activated partial thromboplastin time (APTT), fibrinogen (FIB), antithrombin III (ATIII), lactate (tact), thrombin-antithrombin complex (TAT), α2-plasmin inhibitor/plasmin complex (PIC), protein C (PC), thrombomodulin (TM), and tissue plasminogen activator (tPA)/plasminogen activator inhibitor (PAI-1) complex (Total PAI-1)] were confirmed, each combination of sCD14-ST with D-dimer (Tables 8-10), of sCD14-ST with FDP (Tables 11-13), of sCD14-ST with platelet (Tables 14-15), and of sCD14-ST with TAT (Tables 16-18) was used to evaluate the detection performance of the infectious DIC. The cutoff value of sCD14-ST was set based on the values obtained in Example 12 or 13. As the cutoff value of D-dimer, 6.18 μg/mL, which had been widely used, conventionally, or 10 μg/mL, which was calculated and set in a similar fashion to that of Example 13, were used. As the cutoff value of FDP, 25 μg/mL, which had been widely used, conventionally, or 35 μg/mL, which was calculated and set in a similar fashion to that of Example 13, were used. As the cutoff value of platelet, $12 \times 10^4$ cells/μL, which had been widely used, conventionally, was used. As the cutoff value of TAT, 10 ng/mL, which had been widely used, conventionally, or 26 ng/mL, which was calculated and set in a similar fashion to that of Example 13, were used. For evaluation, clinical sensitivity, specificity, negative predictive value, and positive predictive value under each condition were calculated.

(A) D-dimer

TABLE 8

| | Cutoff value which have been conventionally widely used: 6.18 μg/mL | | | | | |
|---|---|---|---|---|---|---|
| | sCD14-ST | | | | | |
| | <600 | | 600-900 | | ≥900 | |
| | D-dimer | | | | | |
| | <6.18 | ≥6.18 | <6.18 | ≥6.18 | <6.18 | ≥6.18 |
| Cases | 9 | 7 | 4 | 2 | 5 | 17 |
| Percentage (cases) | | | | | | |
| Presence or absence of infection | 44% (4/9) | 29% (2/7) | 100% (4/4) | 50% (1/2) | 80% (4/5) | 94% (16/17) |
| JAAM DIC | 0% (0/9) | 14% (1/7) | 0% (0/4) | 50% (1/2) | 60% (3/5) | 82% (14/17) |
| JAAM DIC (infectious) | 0% (0/9) | 0% (0/7) | 0% (0/4) | 0% (0/2) | 40% (2/5) | 76% (13/17) |
| 28-day mortality | 11% (1/9) | 0% (0/7) | 25% (1/4) | 0% (0/2) | 40% (2/5) | 18% (3/17) |
| Presence or absence of anticoagulant therapy implementation | 11% (1/9) | 0% (0/7) | 25% (1/4) | 0% (0/2) | 40% (2/5) | 35% (6/17) |

TABLE 9

| | Cutoff value obtained in a similar fashion to that of Example 13: 10 μg/mL | | | | | |
|---|---|---|---|---|---|---|
| | sCD14-ST | | | | | |
| | <600 | | 600-900 | | ≥900 | |
| | D-dimer | | | | | |
| | <10 | ≥10 | <10 | ≥10 | <10 | ≥10 |
| Cases | 12 | 4 | 4 | 2 | 8 | 14 |
| Percentage (cases) | | | | | | |
| Presence or absence of infection | 60% (6/12) | 0% (0/4) | 100% (4/4) | 50% (1/2) | 88% (7/8) | 93% (13/14) |
| JAAM DIC | 0% (0/12) | 25% (1/4) | 0% (0/4) | 50% (1/2) | 38% (3/8) | 100% (14/14) |
| JAAM DIC (infectious) | 0% (0/12) | 0% (0/4) | 0% (0/4) | 0% (0/2) | 25% (2/8) | 93% (13/14) |
| 28-day mortality | 10% (1/12) | 0% (0/4) | 25% (1/4) | 0% (0/2) | 25% (2/8) | 21% (3/14) |
| Presence or absence of anticoagulant therapy implementation | 10% (1/12) | 0% (0/4) | 25% (1/4) | 0% (0/2) | 38% (3/8) | 36% (5/14) |

TABLE 10

Clinical sensitivity, specificity, negative predictive value, and positive predictive value in each detection method

| Condition | Method | sCD14-ST (pg/mL) | D-dimer (μg/mL) | Infectious DIC (positive) Test positive | Infectious DIC (positive) Test negative | Infectious DIC (negative) Test positive | Infectious DIC (negative) Test negative | Sensitivity | Specificity | Negative predictive value | Positive predictive value |
|---|---|---|---|---|---|---|---|---|---|---|---|
| 1 | Alone | 600≤ | — | 15 | 0 | 13 | 16 | 100.0% | 55.2% | 100.0% | 53.6% |
| 2 | Alone | 900≤ | — | 15 | 0 | 7 | 22 | 100.0% | 75.9% | 100.0% | 68.2% |
| 3 | Alone | — | 6.18≤ | 13 | 2 | 13 | 16 | 86.7% | 55.2% | 88.9% | 50.0% |
| 4 | Alone | — | 10≤ | 13 | 2 | 7 | 22 | 86.7% | 75.9% | 91.7% | 65.0% |
| 5 | Comb. | 600≤ | 6.18≤ | 13 | 2 | 6 | 23 | 86.7% | 79.3% | 92.0% | 68.4% |
| 6 | Comb. | 900≤ | 6.18≤ | 13 | 2 | 4 | 25 | 86.7% | 86.2% | 92.6% | 76.5% |
| 7 | Comb. | 600≤ | 10≤ | 13 | 2 | 3 | 26 | 86.7% | 89.7% | 92.9% | 81.3% |
| 8 | Comb. | 900≤ | 10≤ | 13 | 2 | 1 | 28 | 86.7% | 96.6% | 93.3% | 92.9% |

Comb.: Combination (B) Fibrin/Fibrinogen Degradation Products (FDP)

TABLE 11

Cutoff value which have been conventionally widely used: 25 μg/mL

| | sCD14-ST | | | | | |
|---|---|---|---|---|---|---|
| | <600 | | 600-900 | | ≥900 | |
| | FDP | | | | | |
| | <25 | ≥25 | <25 | ≥25 | <25 | ≥25 |
| Cases Percentage (cases) | 14 | 2 | 4 | 2 | 9 | 13 |
| Presence or absence of infection | 43% (6/14) | 0% (0/2) | 100% (4/4) | 50% (1/2) | 78% (7/9) | 100% (13/13) |
| JAAM DIC | 0% (0/14) | 50% (1/2) | 0% (0/4) | 50% (1/2) | 56% (5/9) | 92% (12/13) |
| JAAM DIC (infectious) | 0% (0/14) | 0% (0/2) | 0% (0/4) | 0% (0/2) | 33% (3/9) | 92% (12/13) |
| 28-day mortality | 7% (1/14) | 0% (0/2) | 25% (1/4) | 0% (0/2) | 33% (3/9) | 15% (2/13) |
| Presence or absence of anticoagulant therapy implementation | 7% (1/14) | 0% (0/2) | 25% (1/4) | 0% (0/2) | 44% (4/9) | 31% (4/13) |

TABLE 12

Cutoff value obtained in a similar fashion to that of Example 13: 35 μg/mL

| | sCD14-ST | | | | | |
|---|---|---|---|---|---|---|
| | <600 | | 600-900 | | ≥900 | |
| | FDP | | | | | |
| | <35 | ≥35 | <35 | ≥35 | <35 | ≥35 |
| Cases Percentage (cases) | 14 | 2 | 4 | 2 | 10 | 12 |
| Presence or absence of infection | 43% (6/14) | 0% (0/2) | 100% (4/4) | 50% (1/2) | 80% (8/10) | 100% (12/12) |
| JAAM DIC | 0% (0/14) | 50% (1/2) | 0% (0/4) | 50% (1/2) | 50% (5/10) | 100% (12/12) |
| JAAM DIC (infectious) | 0% (0/14) | 0% (0/2) | 0% (0/4) | 0% (0/2) | 30% (3/10) | 100% (12/12) |
| 28-day mortality | 7% (1/14) | 0% (0/2) | 25% (1/4) | 0% (0/2) | 30% (3/10) | 17% (2/12) |

TABLE 12-continued

Cutoff value obtained in a similar fashion to that of Example 13: 35 μg/mL

| | sCD14-ST | | | | | |
|---|---|---|---|---|---|---|
| | <600 | | 600-900 | | ≥900 | |
| | FDP | | | | | |
| | <35 | ≥35 | <35 | ≥35 | <35 | ≥35 |
| Presence or absence of anticoagulant therapy implementation | 7% (1/14) | 0% (0/2) | 25% (1/4) | 0% (0/2) | 40% (4/10) | 33% (4/12) |

TABLE 13

Clinical sensitivity, specificity, negative predictive value, and positive predictive value in each detection method

| | | | | Cases | | | | | | | |
|---|---|---|---|---|---|---|---|---|---|---|---|
| | | Detection method | | Infectious DIC (positive) | | Infectious DIC (negative) | | | | Negative | Positive |
| Condition | Method | sCD14-ST (pg/mL) | FDP (μg/mL) | Test positive | Test negative | Test positive | Test negative | Sensitivity | Specificity | predictive value | predictive value |
| 1 | Alone | 600≤ | — | 15 | 0 | 13 | 16 | 100.0% | 55.2% | 100.0% | 53.6% |
| 2 | Alone | 900≤ | — | 15 | 0 | 7 | 22 | 100.0% | 75.9% | 100.0% | 68.2% |
| 9 | Alone | — | 25≤ | 12 | 3 | 4 | 25 | 80.0% | 82.8% | 88.9% | 70.6% |
| 10 | Alone | — | 35≤ | 12 | 3 | 5 | 24 | 80.0% | 86.2% | 89.3% | 75.0% |
| 11 | Comb. | 600≤ | 25≤ | 12 | 3 | 3 | 26 | 80.0% | 89.7% | 89.7% | 80.0% |
| 12 | Comb. | 900≤ | 25≤ | 12 | 3 | 1 | 28 | 80.0% | 96.6% | 90.3% | 92.3% |
| 13 | Comb. | 600≤ | 35≤ | 12 | 3 | 2 | 27 | 80.0% | 93.1% | 90.0% | 85.7% |
| 14 | Comb. | 900≤ | 35≤ | 12 | 3 | 0 | 29 | 80.0% | 100.0% | 90.6% | 100.0% |

Comb.: Combination (C) Platelet (Plt)

TABLE 14

Cutoff value which have been conventionally widely used: $12 \times 10^4$ cells/μL

| | sCD14-ST | | | | | |
|---|---|---|---|---|---|---|
| | <600 | | 600-900 | | ≥900 | |
| | Plt | | | | | |
| | <12 | ≥12 | <12 | ≥12 | <12 | ≥12 |
| Cases Percentage (cases) | 1 | 15 | 0 | 6 | 11 | 11 |
| Presence or absence of infection | 100% (1/1) | 33% (5/15) | 0% (0/0) | 83% (5/6) | 82% (9/11) | 100% (11/11) |
| JAAM DIC | 0% (0/1) | 7% (1/15) | 0% (0/0) | 17% (1/6) | 100% (11/11) | 55% (6/11) |
| JAAM DIC (infectious) | 0% (0/1) | 0% (0/15) | 0% (0/0) | 0% (0/6) | 82% (9/11) | 55% (6/11) |
| 28-day mortality | 0% (0/1) | 7% (1/15) | 0% (0/0) | 17% (1/6) | 45% (5/11) | 0% (0/11) |
| Presence or absence of anticoagulant therapy implementation | 0% (0/1) | 7% (1/15) | 0% (0/0) | 17% (1/6) | 45% (5/11) | 27% (3/11) |

TABLE 15

Clinical sensitivity, specificity, negative predictive value, and positive predictive value in each detection method

| Condition | Method | Detection method sCD14-ST (pg/mL) | Plt (×10⁴/μL) | Cases Infectious DIC (positive) Test positive | Test negative | Infectious DIC (negative) Test positive | Test negative | Sensitivity | Specificity | Negative predictive value | Positive predictive value |
|---|---|---|---|---|---|---|---|---|---|---|---|
| 1 | Alone | 600≤ | — | 15 | 0 | 13 | 16 | 100.0% | 55.2% | 100.0% | 53.6% |
| 2 | Alone | 900≤ | — | 15 | 0 | 7 | 22 | 100.0% | 75.9% | 100.0% | 68.2% |
| 15 | Alone | — | <12 | 9 | 6 | 3 | 26 | 60.0% | 89.7% | 81.3% | 75.0% |
| 16 | Comb. | 600≤ | <12 | 9 | 6 | 2 | 27 | 60.0% | 93.1% | 81.8% | 81.8% |
| 17 | Comb. | 900≤ | <12 | 9 | 6 | 2 | 27 | 60.0% | 93.1% | 81.8% | 81.8% |

Comb.: Combination (D) Thrombin-Antithrombin Complex (TAT)

TABLE 16

Cutoff value which have been conventionally widely used: 10 ng/mL

| | sCD14-ST <600 | | sCD14-ST 600-900 | | sCD14-ST ≥900 | |
|---|---|---|---|---|---|---|
| | TAT <10 | TAT ≥10 | TAT <10 | TAT ≥10 | TAT <10 | TAT ≥10 |
| Cases | 4 | 12 | 4 | 2 | 5 | 17 |
| Percentage (cases) | | | | | | |
| Presence or absence of infection | 50% (2/4) | 33% (4/12) | 100% (4/4) | 50% (1/2) | 80% (4/5) | 94% (16/17) |
| JAAM DIC | 0% (0/4) | 8% (1/12) | 0% (0/4) | 50% (1/2) | 40% (2/5) | 88% (15/17) |
| JAAM DIC (infectious) | 0% (0/4) | 0% (0/12) | 0% (0/4) | 0% (0/2) | 20% (1/5) | 82% (14/17) |
| 28-day mortality | 25% (1/4) | 0% (0/12) | 25% (1/4) | 0% (0/2) | 0% (0/5) | 29% (5/17) |
| Presence or absence of anticoagulant therapy implementation | 0% (0/4) | 8% (1/12) | 25% (1/4) | 0% (0/2) | 40% (2/5) | 35% (6/17) |

TABLE 17

Cutoff value obtained in a similar fashion to that of Example 13: 26 ng/mL

| | sCD14-ST <600 | | sCD14-ST 600-900 | | sCD14-ST ≥900 | |
|---|---|---|---|---|---|---|
| | TAT <26 | TAT ≥26 | TAT <26 | TAT ≥26 | TAT <26 | TAT ≥26 |
| Cases | 11 | 5 | 4 | 2 | 10 | 12 |
| Percentage (cases) | | | | | | |
| Presence or absence of infection | 45% (5/11) | 20% (1/5) | 100% (4/4) | 50% (1/2) | 90% (9/10) | 92% (11/12) |
| JAAM DIC | 0% (0/11) | 20% (1/5) | 0% (0/4) | 50% (1/2) | 50% (5/10) | 100% (12/12) |
| JAAM DIC (infectious) | 0% (0/11) | 0% (0/5) | 0% (0/4) | 0% (0/2) | 40% (4/10) | 92% (11/12) |
| 28-day mortality | 9% (1/11) | 0% (0/5) | 25% (1/4) | 0% (0/2) | 0% (0/10) | 42% (5/12) |

TABLE 17-continued

Cutoff value obtained in a similar fashion to that of Example 13: 26 ng/mL

| | sCD14-ST | | | | | |
|---|---|---|---|---|---|---|
| | <600 | | 600-900 | | ≥900 | |
| | TAT | | | | | |
| | <26 | ≥26 | <26 | ≥26 | <26 | ≥26 |
| Presence or absence of anticoagulant therapy implementation | 9% (1/11) | 0% (0/5) | 25% (1/4) | 0% (0/2) | 0% (0/10) | 33% (4/12) |

TABLE 18

Clinical sensitivity, specificity, negative predictive value, and positive predictive value in each detection method

| | | | | Cases | | | | | | | |
|---|---|---|---|---|---|---|---|---|---|---|---|
| | | | | Infectious DIC (positive) | | Infectious DIC (negative) | | | | Negative | Positive |
| | Detection method | | | | | | | | | predictive | predictive |
| Condition | Method | sCD14-ST (pg/mL) | TAT (ng/mL) | Test positive | Test negative | Test positive | Test negative | Sensitivity | Specificity | value | value |
| 1 | Alone | 600≤ | — | 15 | 0 | 13 | 16 | 100.0% | 55.2% | 100.0% | 53.6% |
| 2 | Alone | 900≤ | — | 15 | 0 | 7 | 22 | 100.0% | 75.9% | 100.0% | 68.2% |
| 18 | Alone | — | 10≤ | 14 | 1 | 17 | 12 | 93.3% | 41.4% | 92.3% | 45.2% |
| 19 | Alone | — | 26≤ | 11 | 4 | 8 | 21 | 73.3% | 72.4% | 84.0% | 57.9% |
| 20 | Comb. | 600≤ | 10≤ | 14 | 1 | 5 | 24 | 93.3% | 82.8% | 96.0% | 73.7% |
| 21 | Comb. | 900≤ | 10≤ | 14 | 1 | 3 | 26 | 93.3% | 89.7% | 96.3% | 82.4% |
| 22 | Comb. | 600≤ | 26≤ | 11 | 4 | 3 | 26 | 73.3% | 89.7% | 86.7% | 78.6% |
| 23 | Comb. | 900≤ | 26≤ | 11 | 4 | 1 | 28 | 73.3% | 96.6% | 87.5% | 91.7% |

Comb.: Combination

As a result, with respect to each of the detection methods using sCD14-ST alone or a coagulation-related marker (D-dimer, FDP, platelet, or TAT) alone, the clinical sensitivity was high, but the specificity was low. On the other hand, when sCD14-ST was combined with a coagulation-related marker, the clinical sensitivity did not change, but the specificity was evaluated. From these results, it was confirmed that the clinical sensitivity and the specificity became 80% or more by using any one of the combinations of sCD14-ST with D-dimer, of sCD14-ST with FDP, and of sCD14-ST with TAT, for infectious DIC detection, and that these combinations were indexes with high clinical sensitivity and specificity which could not be achieved by conventional indexes, and were very useful.

Comparative Example 1: Evaluation of the Combination of PCT with TAT for the Detection Performance of Infectious DIC With respect to the same 44 cases as those in Example 15, the combination of procalcitonin (PCT) with thrombin-antithrombin complex (TAT) was used to evaluate the detection performance of infectious DIC (Tables 19-20). As the cutoff value of PCT, 0.5 ng/mL and 2.0 ng/mL, which had been widely used, conventionally, were used. As the cutoff value of TAT, 10 ng/mL, which had been widely used, conventionally, was used. For evaluation, clinical sensitivity, specificity, negative predictive value, and positive predictive value under each condition were calculated.

TABLE 19

| | | PCT | | | | |
|---|---|---|---|---|---|---|
| | <0.5 | | 0.5-2.0 | | ≥2.0 | |
| | TAT | | | | | |
| | <10 | ≥10 | <10 | ≥10 | <10 | ≥10 |
| Cases Percentage (cases) | 5 | 10 | 1 | 8 | 7 | 13 |
| Presence or absence of infection | 60% (3/5) | 40% (4/10) | 100% (1/1) | 50% (4/8) | 86% (6/7) | 100% (13/13) |
| JAAM DIC | 0% (0/5) | 30% (3/10) | 0% (0/1) | 50% (4/8) | 29% (2/7) | 77% (10/13) |
| JAAM DIC (infectious) | 0% (0/5) | 20% (2/10) | 0% (0/1) | 25% (2/8) | 14% (1/7) | 77% (10/13) |

TABLE 19-continued

| | PCT | | | | | |
|---|---|---|---|---|---|---|
| | <0.5 | | 0.5-2.0 | | ≥2.0 | |
| | TAT | | | | | |
| | <10 | ≥10 | <10 | ≥10 | <10 | ≥10 |
| 28-day mortality | 20% (1/5) | 10% (1/10) | 0% (0/1) | 0% (0/8) | 14% (1/7) | 31% (4/13) |
| Presence or absence of anticoagulant therapy implementation | 20% (1/5) | 10% (1/10) | 0% (0/1) | 13% (1/8) | 29% (2/7) | 46% (6/13) |

TABLE 20

Clinical sensitivity, specificity, negative predictive value, and positive predictive value in each detection method

| | | | | Cases | | | | | | |
|---|---|---|---|---|---|---|---|---|---|---|
| | | | | Infectious DIC (positive) | | Infectious DIC (negative) | | | | Negative | Positive |
| Condition | Detection method Method | PCT (ng/mL) | TAT (ng/mL) | Test positive | Test negative | Test positive | Test negative | Sensitivity | Specificity | predictive value | predictive value |
| 24 | Alone | 0.5≤ | — | 13 | 2 | 16 | 13 | 86.7% | 44.8% | 86.7% | 44.8% |
| 25 | Alone | 2.0≤ | — | 11 | 4 | 9 | 20 | 73.3% | 69.0% | 83.3% | 55.0% |
| 18 | Alone | — | 10≤ | 14 | 1 | 17 | 12 | 93.3% | 41.4% | 92.3% | 45.2% |
| 27 | Comb. | 0.5≤ | 10≤ | 12 | 3 | 9 | 20 | 80.0% | 69.0% | 87.0% | 57.1% |
| 28 | Comb. | 2.0≤ | 10≤ | 10 | 5 | 3 | 26 | 66.7% | 89.7% | 83.9% | 76.9% |

Comb.: Combination

As a result, there were no conditions in which both the clinical sensitivity and the specificity complied with 80% or more in the method of detecting infectious DIC using the combination of PCT with TAT, and its performance was inferior to that of the combination of sCD14-ST with TAT in Example 15. It was shown that sCD14-ST was useful in detecting infectious DIC, in comparison with PCT, which was known as a conventional sepsis marker.

<<Subjects to be Tested 2>>

The subjects to be tested in Examples 16 to 20 were as follows:

With respect to 87 cases that had been registered in a single facility for clinical practice, on the basis of the criteria similar to those described in "Subjects to be tested 1", evaluation was carried out. Among these cases, disease names were determined in 84 cases. More particularly, systemic inflammatory response syndrome (SIRS) without infection was 19 cases, sepsis was 8 cases, severe sepsis was 14 cases, septic shock was 21 cases, noninfectious diseases (a state of neither infection nor SIRS) were 12 cases, and infectious diseases (a state of infection without SIRS) were 10 cases.

Example 16: Multiple Logistic Regression Analysis of Sepsis Markers in DIC

With respect to the 84 cases in which disease names had been determined, multiple logistic regression analysis was carried out. For this analysis, the objective variable was the diagnostic criteria for JAAM DIC (a non-DIC group or a DIC group); the explanatory variables were sCD14-ST, procalcitonin (PCT), interleukin-6 (IL-6), and C-reactive protein (CRP); and a continuous variable was changed by one unit for the unit odds ratio. As a result of the likelihood ratio test for the effect, since the odds ratio was 1.001572, and the 95% CI was 1.000865-1.002446, p<0.0001, sCD14-ST was most useful.

Example 17: Multiple Logistic Regression Analysis of Coagulation-Related Markers in DIC With respect to the 84 cases in which disease names had been determined, multiple logistic regression analysis (stepwise method) was carried out. For this analysis, the objective variable was the diagnostic criteria for JAAM DIC (a non-DIC group or a DIC group); the explanatory variables were antithrombin III (ATIII), protein C (PC), and thrombomodulin (TM); and a continuous variable was changed by one unit for the unit odds ratio. As a result of the likelihood ratio test for the effect, since the odds ratio was 0.944377, and the 95% CI was 0.918842-0.965239, p<0.0001, protein C was most useful.

Example 18: ROC Analysis and Cutoff Value Evaluation of sCD14-ST and PC for Presence or Absence of Sepsis>>

Among the 84 cases in which disease names had been determined, with respect to 80 cases in which all the measured values for sCD14-ST and protein C (PC) were confirmed (sepsis group: 40 cases, and non-sepsis group: 40 cases), ROC analysis was carried out. The AUC of sCD14-ST was 0.925 (p<0.0001), and the AUC of PC was 0.833 (p<0.0001). The cutoff value of sCD14-ST was 647 pg/mL (sensitivity: 93.0%, specificity: 75.6%), and the cutoff value of PC was 47% (sensitivity: 77.5%, specificity: 80.0%). It was considered from these results that the optimal cutoff values were 650 pg/mL (sCD14-ST) and 45% (PC).

Example 19: ROC Analysis and Cutoff Value Evaluation of sCD14-ST and PC for Presence or Absence of DIC>>

Among the 84 cases in which disease names had been determined, with respect to 81 cases in which all the measured values for sCD14-ST and protein C (PC) were confirmed (DIC group: 36 cases, and non-DIC group: 45 cases), ROC analysis was carried out. The AUCs of sCD14-ST and PC were 0.836 (p<0.0001) and 0.891 (p<0.0001), respectively. The cutoff values of sCD14-ST and PC were 899 pg/mL (sensitivity: 81.6%, specificity: 80.9%) and 55% (sensitivity: 89.2%, specificity: 75.6%), respectively. It was considered from these results that the optimal cutoff values of sCD14-ST and PC were 900 pg/mL and 55%, respectively.

Example 20: Evaluation of the Combination of sCD14-ST with PC for the Detection Performance of Infectious DIC>>

Among the 84 cases in which disease names had been determined, with respect to 81 cases in which all the measured values for sCD14-ST and PC were confirmed, the combination of sCD14-ST with PC (Tables 21-22) was used to evaluate the detection performance of infectious DIC in a similar fashion to that of Example 15. The cutoff values were set from the values obtained in Example 18 or 19. For evaluation, clinical sensitivity, specificity, negative predictive value, and positive predictive value under each condition were calculated.

TABLE 21

| | sCD14-ST | | | | | | | | |
|---|---|---|---|---|---|---|---|---|---|
| | <650 | | | 650-900 | | | ≥900 | | |
| | PC | | | | | | | | |
| | <45 | 45-55 | ≥55 | <45 | 45-55 | ≥55 | <45 | 45-55 | ≥55 |
| Cases Percentage (cases) | 2 | 3 | 30 | 7 | 0 | 2 | 28 | 3 | 6 |
| Presence or absence of infection | 0% (0/2) | 33% (1/3) | 27% (8/30) | 71% (5/7) | 0% (0/0) | 50% (1/2) | 96% (27/28) | 67% (2/3) | 83% (5/6) |
| JAAM DIC | 50% (1/2) | 67% (2/3) | 3% (1/30) | 29% (2/7) | 0% (0/0) | 0% (0/2) | 86% (24/28) | 67% (2/3) | 50% (3/6) |
| JAAM DIC (infectious) | 0% (0/2) | 0% (0/3) | 0% (0/30) | 0% (0/7) | 0% (0/0) | 0% (0/2) | 82% (23/28) | 33% (1/3) | 33% (2/6) |
| 28-day mortality | 0% (0/2) | 33% (1/3) | 7% (2/30) | 29% (2/7) | 0% (0/0) | 0% (0/2) | 29% (8/28) | 0% (0/3) | 17% (1/6) |

TABLE 22

Clinical sensitivity, specificity, negative predictive value, and positive predictive value in each detection method

| Condition | Method | Detection method Details | Infectious DIC (positive) Test positive | Infectious DIC (positive) Test negative | Infectious DIC (negative) Test positive | Infectious DIC (negative) Test negative | Sensitivity | Specificity | Negative predictive value | Positive predictive value |
|---|---|---|---|---|---|---|---|---|---|---|
| 29 | Alone | sCD14-ST ≥ 650 pg/mL | 26 | 0 | 20 | 35 | 100.0% | 63.6% | 100.0% | 56.5% |
| 30 | Alone | sCD14-ST > 900 pg/mL | 26 | 0 | 11 | 44 | 100.0% | 80.0% | 100.0% | 70.3% |
| 31 | Alone | PC < 55% | 24 | 2 | 19 | 36 | 92.3% | 65.5% | 94.7% | 55.8% |
| 32 | Alone | PC < 45% | 23 | 3 | 21 | 34 | 88.5% | 61.8% | 91.9% | 52.3% |
| 33 | Comb. | (*1) | 26 | 0 | 20 | 35 | 100.0% | 63.6% | 100.0% | 56.5% |
| 34 | Comb. | sCD14-ST ≥ 900 pg/mL and PC < 45% | 23 | 3 | 5 | 50 | 88.5% | 90.9% | 94.3% | 82.1% |

(*1): (i) When sCD14-ST < 650 pg/mL, PC < 45%; (ii) when sCD14-ST 650-900 pg/mL, PC < 55%; or (iii) sCD14-ST ≥ 900 pg/mL
Comb.: Combination Similar with the results in Example 15, with respect to each detection method using sCD14-ST or PC alone, the clinical sensitivity was high, but the specificity was low. On the other hand, when sCD14-ST was combined with PC, the specificity was evaluated. It was confirmed that the clinical sensitivity and the specificity became 80% or more by using the combination of sCD14-ST with PC for infectious DIC detection, and that this combination was an index with high clinical sensitivity and specificity which could not be achieved by conventional indexes, and was very useful.

Referential Example 1: Usefulness for DIC Diagnosis in Uninfected Group

The uninfected group of Example 12, i.e., the 13 uninfected cases (SIRS and noninfectious diseases), were classified into a DIC group (4 cases) and a non-DIC group (9 cases) on the basis of the diagnostic criteria for JAAM DIC, and the usefulness of sCD14-ST, procalcitonin (PCT), C-reactive protein (CRP), interleukin-6 (IL-6), D-dimer, and fibrin/fibrinogen degradation products (FDP) for DIC detection was compared to one another by ROC analysis.

The measurement of PCT was carried out using ECLusys BRAHMS PCT (Roche Diagnostics). IL-6 was measured using Immulyze IL-6 (Siemens Healthcare Diagnostics, Inc.). CRP was measured using CRP-latex X2 "Seiken" (Denka Seiken Co., Ltd.). Hitachi 7170S (Hitachi High-Technologies Corporation) was used as the measuring apparatus. D-dimer was measured using Nanopia D-dimer (Sekisui Medical Co., Ltd.). Coapresta 2000 (Sekisui Medical Co., Ltd.) was used as the measuring apparatus. FDP was measured using Nanopia p-FDP (Sekisui Medical Co., Ltd.). Coapresta 2000 (Sekisui Medical Co., Ltd.) was used as the measuring apparatus.

Figure 36:
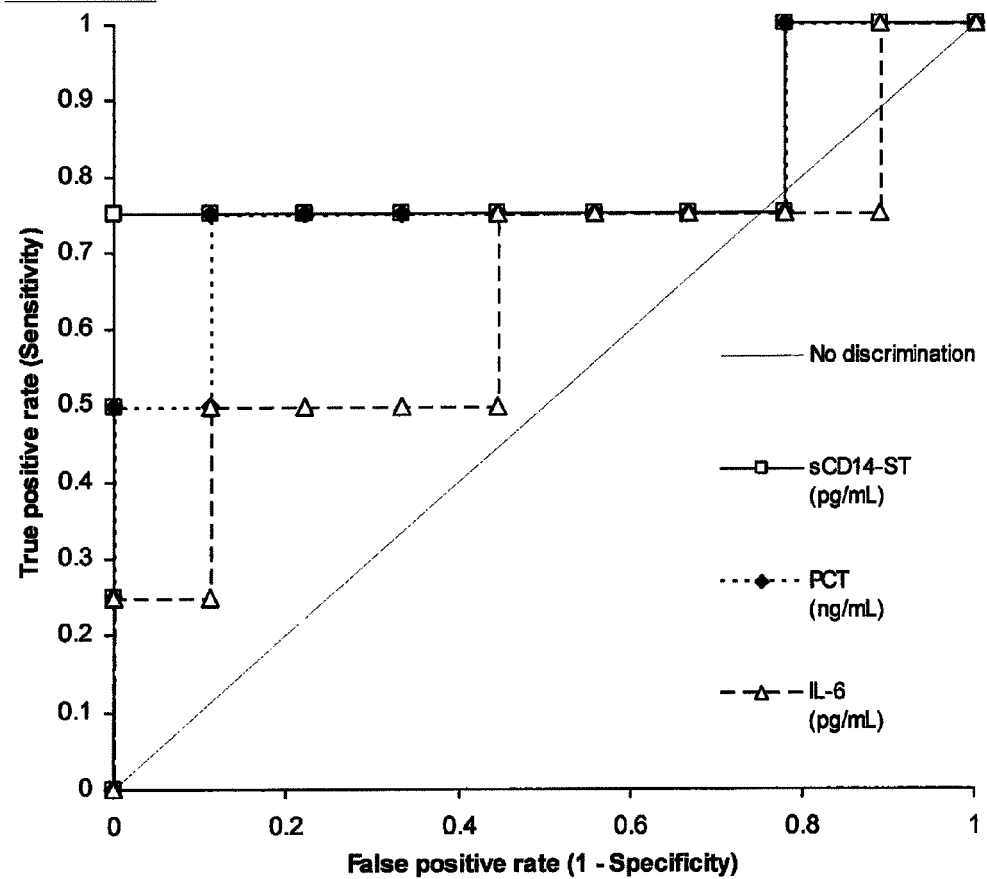
FIG. 36 is a graph showing the results of ROC analysis. Among patients (49 cases) registered in a clinical study, 13 uninfected cases (SIRS and noninfectious diseases) were classified into a DIC group (4 cases) and a non-DIC group (9 cases) on the basis of the diagnostic criteria for JAAM DIC, and each usefulness for DIC detection of sCD14-ST, procalcitonin (PCT), and interleukin-6 (IL-6) in samples collected on admission was compared to one another by ROC analysis.

The results are shown in FIGS. 36 and 37. In FIGS. 36 and 37, the horizontal axis is the "1-specificity", and the vertical axis is "sensitivity".

The calculated AUCs were 0.806 (sCD14-ST), 0.778 (PCT), 0.639 (IL-6), 0.583 (CRP), 0.764 (D-dimer), and 0.792 (FDP), and the AUC of sCD14-ST was the highest. It was confirmed from this result that sCD14-ST was more useful than conventional markers, such as D-dimer, FDP, and the like. When the sCD14-ST value was 600 pg/mL, the clinical sensitivity was 75.0% and the specificity was 100%, and it was considered to be the optimal cutoff value.

INDUSTRIAL APPLICABILITY

The present invention can be employed to detect disseminated intravascular coagulation (DIC), and to grasp its clinical condition. According to the present invention, a patient suffering from DIC can be specified from patients suspected of having DIC, and the status of the DIC patient can be monitored by carrying out the measurement over time, and it is useful to determine an appropriate course of treatment.

Further, the present invention can be employed to detect infectious disseminated intravascular coagulation (infectious DIC), and to grasp its clinical condition. According to the present invention, a patient suffering from infectious DIC can be specified from patients suspected of having infectious DIC, and the status of the infectious DIC patient can be monitored by carrying out the measurement over time, and it is useful to determine an appropriate course of treatment.

Although the present invention has been described with reference to specific embodiments, various changes and modifications obvious to those skilled in the art are possible without departing from the scope of the appended claims.

---

---

The invention claimed is:

1. A method of diagnosing and treating infectious disseminated intravascular coagulation, comprising the steps of:

(A) measuring soluble Cluster of Differentiation 14 subtype (sCD14-ST) in a sample collected from a patient suspected of having disseminated intravascular coagulation, or a patient suffering from disseminated intravascular coagulation;

(B) judging that the patient suffers from disseminated intravascular coagulation when an sCD14-ST value is higher than that of a non-disseminated-intravascular-coagulation patient; and (C) administering an appropriate treatment to the patient for infectious disseminated intravascular coagulation.

2. The method according to claim 1, wherein the sCD14-ST value is compared in the judgment step to a threshold previously determined.

3. The method according to claim 1, wherein sCD14-ST is measured by an immunoassay.

4. The method according to claim 1, comprising measuring a coagulation-related marker in a sample in addition to sCD14-ST.

5. A method of diagnosing and treating infectious disseminated intravascular coagulation, comprising the steps of:
(A) measuring soluble Cluster of Differentiation 14 subtype (sCD14-ST) and a coagulation-related marker in a sample collected from a patient suspected of having infectious disseminated intravascular coagulation, or a patient suffering from infectious disseminated intravascular coagulation, and
(B) judging that the patient suffers from infectious disseminated intravascular coagulation when an sCD14-ST value and a coagulation-related marker value are changed in comparison with those of a non-infectious-disseminated-intravascular-coagulation patient; and
(C) administering an appropriate treatment to the patient for infectious disseminated intravascular coagulation.

6. The method according to claim 5, wherein the sCD14-ST value and the coagulation-related marker value are compared in the judgment step to thresholds previously determined, respectively.

7. The method according to claim 5, wherein the coagulation-related marker is at least one selected from the group consisting of D-dimer, fibrin/fibrinogen degradation products (FDP), thrombin-antithrombin III complex, platelet counts, and protein C.

8. The method according to claim 5, wherein sCD14-ST is measured by an immunoassay.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Homo sapiens

<400> SEQUENCE: 1

Thr Thr Pro Glu Pro Cys Glu Leu Asp Asp Glu
1               5                   10

<210> SEQ ID NO 2
<211> LENGTH: 16
<212> TYPE: PRT
<213> ORGANISM: Homo sapiens

<400> SEQUENCE: 2

Arg Val Asp Ala Asp Ala Asp Pro Arg Gln Tyr Ala Asp Thr Val Lys
1               5                   10                  15
```